US012784906B2

(12) United States Patent
Ausin et al.

(10) Patent No.: US 12,784,906 B2
(45) Date of Patent: Nov. 3, 2026

(54) MULTI-CALL MEMORY TO INTERJECT PREVIOUSLY GATHERED INFORMATION INTO A CONVERSATION BETWEEN AN ARTIFICIAL INTELLIGENCE (AI) AND A HUMAN

(71) Applicant: HealthGPT, Inc., Palo Alto, CA (US)

(72) Inventors: Markel Sanz Ausin, Palo Alto, CA (US); Akash Chaurasia, Palo Alto, CA (US); Alex Miller, Palo Alto, CA (US); Jonathan David Agnew, Palo Alto, CA (US); Rae Lasko, Palo Alto, CA (US); Mariska Raglow-Defranco, Palo Alto, CA (US); Michelle Voisard, Palo Alto, CA (US); Saad Godil, Palo Alto, CA (US); Subhabrata Mukherjee, Palo Alto, CA (US)

(73) Assignee: HealthGPT, Inc., Palo Alto, CA (US)

( * ) Notice: Subject to any disclaimer, the term of this patent is extended or adjusted under 35 U.S.C. 154(b) by 0 days.

(21) Appl. No.: 19/400,096

(22) Filed: Nov. 25, 2025

(65) Prior Publication Data

US 2026/0081010 A1 Mar. 19, 2026

Related U.S. Application Data

(63) Continuation-in-part of application No. 18/900,289, filed on Sep. 27, 2024, which is a continuation of
(Continued)

(51) Int. Cl.
*G10L 15/00* (2013.01)
*G10L 15/183* (2013.01)
(Continued)

(52) U.S. Cl.
CPC ........... *G16H 40/20* (2018.01); *G10L 15/183* (2013.01); *G10L 15/22* (2013.01); *G10L 25/66* (2013.01); *G10L 15/1822* (2013.01); *G10L 15/19* (2013.01)

(58) Field of Classification Search
CPC ......... G10L 15/16; G10L 25/27; G10L 25/30; G10L 19/005; G10L 19/00; G10L 15/02;
(Continued)

(56) References Cited

U.S. PATENT DOCUMENTS 7,284,046 B1 * 10/2007 Kreiner ................ H04L 67/303 455/414.3
8,548,937 B2 10/2013 Saigal et al.
(Continued)

OTHER PUBLICATIONS

Anonymous, Error Handling and Fallback Mechanisms in AI Assistants: A Comprehensive Guide, Nexus Flow Innovations, published on Nov. 11, 2024, 4 pages. Retrieved from the internet on Aug. 8, 2025. URL: https://www.nexusflowinnovations.com/blog/error-handling-fallback-mechanisms-ai-assistants.
(Continued)

*Primary Examiner* — Vu B Hang
(74) *Attorney, Agent, or Firm* — FP; Shiv S Naimpally; Sikander M. Khan

(57) ABSTRACT

A conversational artificial intelligence (AI) system is configured to engage in a multi-turn conversation with a user. The multi-turn conversation is substantially focused on a target topic. A conversation analyzer analyzes the multi-turn conversation to detect and store at least some turns in the multi-turn conversation that deviate from the target topic and instead characterize life attributes of the user. A knowledge graph constructor builds a knowledge graph for the user based on at least some turns in the multi-turn conversation that characterize the life attributes of the user. The knowledge graph translates the life attributes of the user into
(Continued)

the user's life biography, including life chronology, life preferences, life milestones, life events, or any combination thereof. A knowledge graph applicator uses parts of the knowledge graph in a subsequent multi-turn conversation with the user by contextually interspersing portions of the user's life biography in the subsequent multi-turn conversation.

20 Claims, 10 Drawing Sheets

Related U.S. Application Data application No. 18/592,441, filed on Feb. 29, 2024, now Pat. No. 12,142,371.

(60) Provisional application No. 63/828,682, filed on Jun. 23, 2025, provisional application No. 63/611,762, filed on Dec. 18, 2023, provisional application No. 63/466,712, filed on May 15, 2023.

(51) Int. Cl.

| | |
|---|---|
| ***G10L 15/22*** | (2006.01) |
| ***G10L 25/66*** | (2013.01) |
| ***G16H 40/20*** | (2018.01) |
| *G10L 15/18* | (2013.01) |
| *G10L 15/19* | (2013.01) |

(58) Field of Classification Search

CPC ....... G10L 15/063; G10L 15/07; G10L 15/08; G10L 15/20; G10L 15/22; G10L 15/26; G10L 15/30; G10L 15/1822; G10L 15/183; G10L 15/193; G10L 15/19; G10L 17/00; G10L 17/02; G10L 17/04; G10L 17/06; G10L 25/66; G10L 2015/226; G10L 25/33; G16H 40/20; G16H 10/60; G16H 50/20

See application file for complete search history.

(56) References Cited

U.S. PATENT DOCUMENTS

| | | | |
|---|---|---|---|
| 9,824,188 | B2 * | 11/2017 | Brown ................ G06F 3/04886 |
| 10,282,512 | B2 | 5/2019 | Bennett et al. |
| 10,452,816 | B2 | 10/2019 | Kidd et al. |
| 10,504,379 | B2 | 12/2019 | Vinkers et al. |
| 10,748,644 | B2 | 8/2020 | Shriberg et al. |
| 11,329,933 | B1 | 5/2022 | Kiyanda et al. |
| 11,348,694 | B2 | 5/2022 | Kim et al. |
| 11,438,283 | B1 * | 9/2022 | White ................... G06F 40/216 |
| 11,532,393 | B2 | 12/2022 | Arkoff et al. |
| 11,693,990 | B1 | 7/2023 | Arkoff et al. |
| 11,694,807 | B2 | 7/2023 | Golan et al. |
| 11,843,565 | B2 | 12/2023 | Lee et al. |
| 11,977,854 | B2 | 5/2024 | Tunstall-Pedoe et al. |
| 2010/0235899 | A1 * | 9/2010 | Li ....................... G06F 12/0888 726/9 |
| 2014/0365885 | A1 | 12/2014 | Carson et al. |
| 2019/0341052 | A1 | 11/2019 | Allibhai |
| 2020/0137230 | A1 * | 4/2020 | Spohrer .............. H04M 7/0027 |
| 2023/0108637 | A1 * | 4/2023 | Rabinovich ............. G06F 18/22 717/124 |
| 2023/0245651 | A1 | 8/2023 | Wang |
| 2024/0185968 | A1 | 6/2024 | Doerr et al. |

OTHER PUBLICATIONS

Biao et al., Root Mean Square Layer Normalization, School of Informatics, University of Edinburgh, Retrieved on Jun. 6, 2024, 12 pages. [NeurIPS 2019].
Dosovitskiy et al., An Image Is Worth 16x16 Words: Transformers For Image Recognition at Scale, ICLR 2021, dated Jun. 3, 2021, 22 pages.
Gao et al. Retrieval-Augmented Generation for Large Language Models: A Survey, Shanghai Research Institute for Intelligent Autonomous Systems, Tongji University, Mar. 27, 2024, 21 pages. [URL: arXiv:2312.10997].
Karan et al., Large Language Models Encode Clinical Knowledge, Google Research, Dec. 26, 2022, 44 pages. [arXiv:2212.13138].
McGreevy et al., Clinical, Legal, and Ethical Aspects of Artificial Intelligence-Assisted Conversational Agents in Health Care, JAMA, vol. 324, No. 6, dated Aug. 11, 2020, 2 pages.
Peter et al., Benefits, Limits, and Risks of GPT-4 as an AI Chatbot for Medicine. The New England Journal of Medicine, Mar. 30, 2023, 7 pages [N Engl Med 388;13].
PGR2025-00075—Mandatory Notices, filed on 2025-08-25, 4 pages.
PGR2025-00075—Petition for Post-Grant Review Updated, filed on Aug. 12, 2025, 83 pages.
PGR2025-00075—Petition for Post-Grant Review Updated, filed on Aug. 27, 2025, 4 pages.
PGR2025-00075—Petition for Post-Grant Review Updated, filed on Aug. 27, 2025, 83 pages.
Surani et al., Understanding Privacy and Security Postures of Healthcare Chatbots, CHI-22, Apr. 30-May 6, 2022, 7 pages.
Tao et al., Towards Conversational Diagnostic AI, Google Research, Jan. 11, 2024, 46 pages. [arXiv:2401.05654].
Vaswani et al., Attention Is All You Need, Advances in Neural Information Processing Systems 2017, dated Dec. 6, 2017, 15 pages.

* cited by examiner

MULTI-CALL MEMORY TO INTERJECT PREVIOUSLY GATHERED INFORMATION INTO A CONVERSATION BETWEEN AN ARTIFICIAL INTELLIGENCE (AI) AND A HUMAN

PRIORITY DATA

The present non-provisional patent application claims priority to and the benefit from (1) U.S. Application 63/828,682 filed on Jun. 23, 2025, and (2) U.S. application Ser. No. 18/900,289 filed on Sep. 27, 2024, which is incorporated herein by reference in their entirety and for all purposes as if completely and fully set forth herein.

BACKGROUND OF THE TECHNOLOGY DISCLOSED

Field of the Technology Disclosed

The technology disclosed relates to artificial intelligence type computers and digital data processing systems and corresponding data processing methods and products for emulation of intelligence (i.e., knowledge-based systems, reasoning systems, and knowledge acquisition systems); and including systems for reasoning with uncertainty (e.g., fuzzy logic systems), adaptive systems, machine learning systems, and artificial neural networks. In particular, the technology disclosed relates generally to systems and techniques, including using multi-call memory, to interject previously gathered information during a conversation between an artificial intelligence (AI) agent and a human patient. The information is interjected based on its relevance to a context of the conversation.

Description of the Related Art

Current AI virtual assistants (which include chat bots), such as ChatGPT and the like, are not designed for use in healthcare fields and so have a variety of issues. For example, current AI virtual assistants are incapable of following a checklist, are too verbose for multi-turn conversations, and are not designed to comply with medical safety laws, regulations, and procedures. One issue is that an AI virtual assistant does not personalize the conversation in the way that a human would do when conversing with another human.

SUMMARY OF THE TECHNOLOGY DISCLOSED

This Summary provides a simplified form of concepts that are further described below in the Detailed Description. This Summary is not intended to identify key or essential features and should therefore not be used for determining or limiting the scope of the claimed subject matter.

In some aspects, a conversational artificial intelligence (AI) system includes a large language model (LLM) configured to execute and store a multi-turn conversation with a user, in a memory device. The multi-turn conversation is substantially focused on a target topic. A conversation analyzer has access to the memory device and analyzes the multi-turn conversation to detect and store at least some turns in the multi-turn conversation that deviate from the target topic and instead characterize life attributes of the user. A knowledge graph constructor builds a knowledge graph associated with the user based on at least some turns in the multi-turn conversation that characterize the life attributes of the user and stores the knowledge graph in the memory. The knowledge graph translates the life attributes of the user into the user's life biography, including life chronology, life preferences, life milestones, life events, or any combination thereof. A knowledge graph applicator uses parts of the knowledge graph in a subsequent multi-turn conversation with the user. Selection of the parts of the knowledge graph is based on a current context of the subsequent multi-turn conversation. The knowledge graph applicator uses parts of the knowledge graph in the subsequent multi-turn conversation by contextually interspersing portions of the user's life biography in the subsequent multi-turn conversation.

BRIEF DESCRIPTION OF THE DRAWINGS

A more complete understanding of the present disclosure may be obtained by reference to the following Detailed Description when taken in conjunction with the accompanying Drawings. In the figures, the left-most digit(s) of a reference number identifies the figure in which the reference number first appears. The same reference numbers in different figures indicate similar or identical items.

DETAILED DESCRIPTION

Introduction

Figure 1:
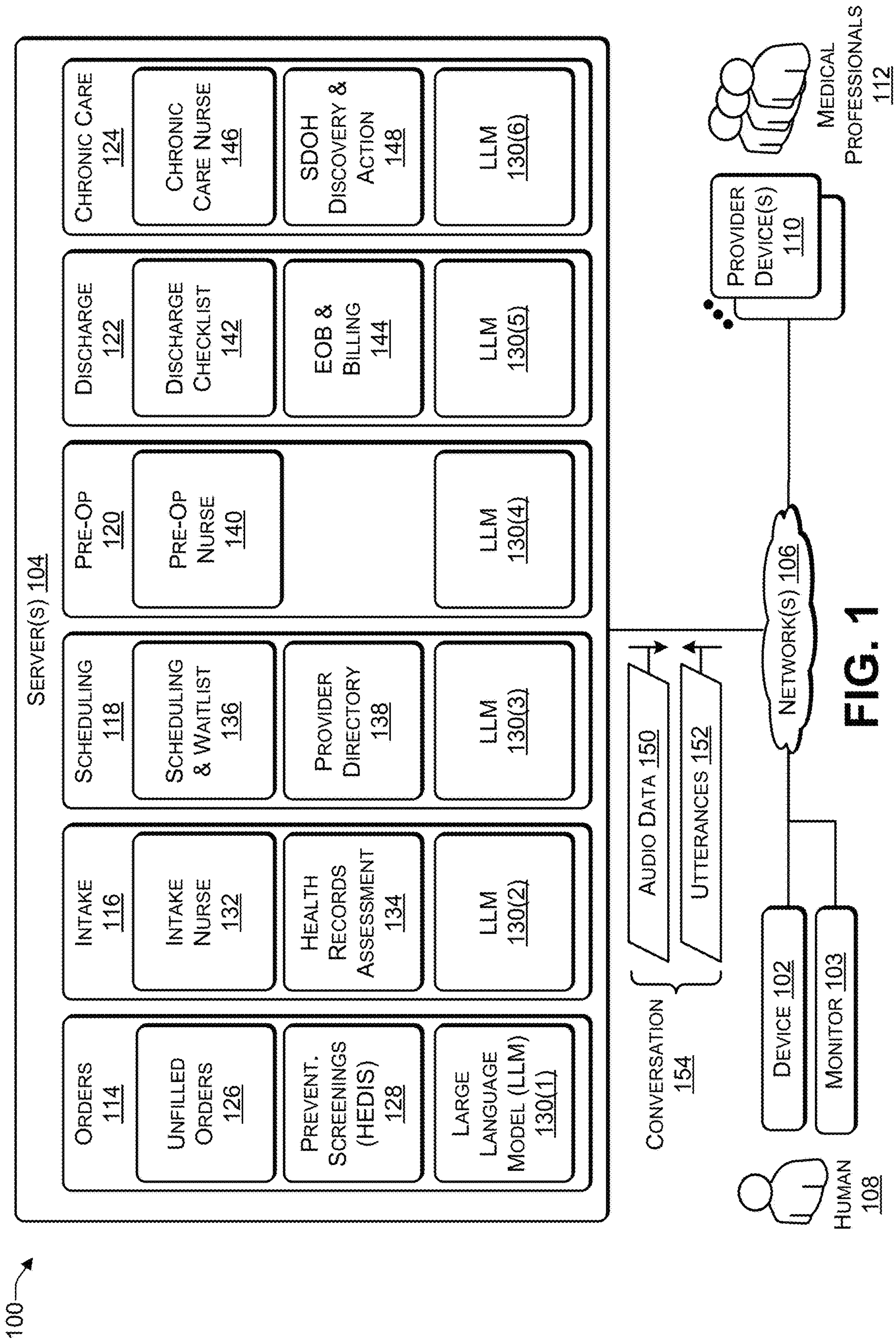
FIG. 1 is a block diagram of a system illustrating large language models (LLMs) to perform specialized healthcare-related functions, according to some implementations.

The disclosed agentic AI architecture for multi-call, healthcare-focused conversations constitutes a materially different and technically advanced class of conversational AI systems. Unlike generic virtual assistants that treat each interaction as an isolated, stateless exchange, the technology disclosed introduces an explicit multi-call memory substrate that reorganizes how large language models (LLMs) acquire, structure, and reuse information about a user across multiple conversations. A conversation analyzer processes a preceding multi-turn conversation that is substantially focused on a target topic (for example, a healthcare-related topic), detects turns that deviate from the target topic and instead characterize "life attributes" of the user, and stores those turns in memory as non-medical but biographically meaningful data. A knowledge graph constructor then builds a user-specific knowledge graph that translates these life attributes into a structured life biography, including life chronology, life preferences, life milestones, and life events. A knowledge graph applicator, operating in conjunction with the underlying LLMs, selects contextually relevant parts of this biography in a subsequent multi-turn conversation and contextually intersperses portions of the user's life biography into ongoing dialogue. These components do not merely tag transcripts; they form a runtime control layer that directly conditions how the underlying LLMs plan, parameterize, and execute each response based on a persistent, machine-actionable representation of the user.

At the level of computer functionality, this architecture provides a specific, technical improvement to both the underlying LLMs and the computing platform that executes them. The knowledge graph is stored in a tokenized format, for example as key-value (KV) entries in a cache and associated memory, so that portions of the user's biography can be retrieved and injected into the underlying LLMs' context without re-encoding entire prior conversations. Instead of forcing the model to repeatedly process long, unstructured text histories, the system retrieves only the minimal token sequences and embeddings corresponding to the relevant nodes and edges of the knowledge graph. This reduces redundant encoding work, lowers GPU/accelerator load per response, decreases pressure on high-bandwidth memory (HBM) and dynamic random-access memory (DRAM), and shortens the effective context length required for each turn. By structuring memory access around pre-computed, patient-specific vectors and tokenized graph fragments rather than raw conversational logs, the system improves cache locality and reduces traffic over internal system buses when serving long, safety-critical healthcare dialogues.

The multi-call memory mechanisms also address a concrete limitation of transformer-based LLMs in long-duration settings: context-window saturation and instability in very long conversations. The system segments preceding multi-turn conversations into semantically meaningful units (for example, turns focused on life attributes versus turns focused on the target medical topic), encodes those units into embeddings, and indexes them so that only life-attribute segments with relevance to the current conversational context are selected. The knowledge graph applicator determines the current context of a subsequent multi-turn conversation, identifies tokenized history that includes relevant non-medical data, and selects that data for inclusion in the subsequent artificial intelligence response. This targeted selection prevents unnecessary expansion of the context window, reduces token churn, and ensures that the KV cache is populated predominantly with high-salience, biography-related tokens rather than verbose, redundant history. As a result, the underlying LLMs can allocate more of their attention budget and compute capacity to the medically and emotionally salient portions of the dialogue while still expressing long-range familiarity with the user.

Technically, the invention improves how data structures supporting patient context are represented, stored, and accessed. Instead of storing "life attributes" as unstructured text blobs in generic databases, the knowledge graph constructor builds a typed graph whose nodes and edges represent life chronology, life preferences, life milestones, life events, and other biography elements. This graph is then translated into tokenized sequences that can be stored in the KV cache and a memory device for low-latency reuse. The knowledge graph applicator operates as an inference-time controller: given the current turn and conversational context, it selects a particular portion of the tokenized history of the conversation that includes non-medical data relevant to that context, and intersperses those tokens into the underlying LLMs' input in a structured way. This design reduces query volume to backing stores, avoids repeated parsing of large, unstructured records, and shortens the critical path between user utterance, context retrieval, and response generation—delivering measurable gains in end-to-end system responsiveness and throughput per accelerator.

From the underlying LLMs' perspective, the disclosed architecture converts an otherwise stateless conversational interface into a multi-call, pre-acquainted agent that is explicitly trained and configured to create, update, and exploit multi-call memory. The underlying LLMs are configured not only to execute multi-turn conversations substantially focused on target healthcare topics, but also to collaborate with the conversation analyzer and knowledge graph constructor to identify which turns should be elevated into long-term life-attribute memory, and with the knowledge graph applicator to decide when and how to weave those memories into subsequent exchanges. This restructures inference as a sequence of memory-aware sub-tasks—detection of off-topic life attributes, graph update, memory selection based on current context, and contextual interspersion of biography-rather than a flat, token-by-token generation loop. In practice, this leads to fewer tokens per turn devoted to reconstructing background information, more computational budget for clinical reasoning and empathetic dialogue, and more stable behavior in multi-session conversations under fixed hardware and context-window constraints.

The technical benefits are particularly pronounced in the healthcare setting, where conversations are long, repeated, and safety-critical, and where Hippocratic AI deploys constellations of role-specific virtual assistants (for example, intake, chronic care, discharge, and scheduling agents) over shared infrastructure. By precomputing and caching key life attributes and knowledge-graph fragments, the architecture reduces the need for repeated full-model passes over historical transcripts or external biographic sources when a patient reconnects with any of these role-specific assistants. The tokenized knowledge graph stored in a KV cache can be accessed by different assistants serving different roles, enabling consistent familiarity and rapport without duplicative processing or storage. This lowers total accelerator utilization, allows the same hardware cluster to support more concurrent patient sessions, and provides a stable substrate on which multiple Hippocratic AI agents can safely express familiarity and continuity across calls.

In sum, the Hippocratic AI multi-call memory and knowledge-graph architecture delivers a concrete, hardware-observable improvement to computer technology in the context of healthcare conversational systems. It reduces computational redundancy, improves KV-cache and memory utilization, mitigates long-context pathologies in transformer models, and lowers end-to-end latency for complex, multi-turn conversations with returning patients. At the same time, it enables a new class of pre-acquainted conversational agents that can express genuine familiarity grounded in structured life biographies, rather than ad hoc prompts or fragile session stitching. These characteristics align with and extend the agentic AI framework: control is shifted from offline weight updates to inference-time orchestration over structured memory and tools, resulting in a genuinely improved AI computing system tailored to high-stakes, healthcare-grade interactions.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

Despite recent advancements in conversational artificial intelligence (AI) due to large language models (LLMs), there is still a need for thorough evaluation of LLMs' efficacy in handling very long conversations. This evaluation is crucial for constructing conversational AI capable of remembering key information from past interactions, to generate empathetic, friendly, and consistent responses.

The disclosed conversational AI agent uses "multi-call memory" to conduct real-world conversations with a returning caller that are a complex blend of collective memories, external influences, and the unique persona of the returning caller. The disclosed conversational AI agent creates a knowledge graph of the returning caller's life based on past conversations and recalls past context correctly from the knowledge graph to integrate relevant information into future responses to make them empathetic and friendly and consistent with the ongoing narrative. What results is AI-driven conversations that parallel how humans remember recent conversations while also recalling distilled important experiences from long-term memory. In a health care context, the disclosed conversational AI detects and stores "non-medical memories/nuggets" about a patient's life in the patient's knowledge graph and selectively interjects them in subsequent medical conversations with the patient to make the patient's conversational experience more like a human-to-human conversation.

Tokenization

Before processing, text input received from an ASR may be divided into smaller units, called tokens. For example, "I am John" may be split into 3 tokens: "I", "am", and "John". As another example, "See John run" may be tokenized as "See", "John", and "run" based on a dictionary. An AI model converts the input into tokens using a process known as tokenization. For an AI model, such as a large language model (LLM), short words may be represented with a single token, while longer words may be split into two or more tokens. For example, the word darkness may be split into two tokens, "dark" and "ness," with each token having a corresponding numerical representation, such as 217 and 655. The opposite word, brightness, may similarly be split into "bright" and "ness," with corresponding numerical representations, 491 and 655. In this example, the shared numerical value associated with "ness" helps the AI model understand that the words have something in common. In some cases, a tokenizer may assign different numerical representations for the same word depending on the context. Tokens may also be based on audio or video segments rather than portions of words. The tokens are used to create a conversation history that includes a knowledge graph of medical information and a knowledge graph of non-medical information.

The conversation history may be stored a in a cache, enabling fast access during the conversation to enable the conversation to mimic a conversation between two humans. For example, a Key-Value (KV) cache may be used during the generation (inference) phase. The KV cache stores and retrieves previously computed data (e.g., tokens), helping the AI generate a response quickly, without the AI having to recalculate information (tokens) that the AI has previously processed. The KV cache saves information about the previous conversation, including previously computed internal representations (tokens). When generating a sequence of tokens, the AI computes a key vector and a value vector for each token in a sequence at each step. The KV cache stores the key and value vectors for each token, as they are computed. When generating the next token, the model may reuse the stored key and value vectors for the previous tokens, rather than recomputing them. By reusing the cached values, the KV cache eliminates the need to recalculate the key and value vectors for previous tokens, significantly reducing computational cost and speeding up the generation (output) process. By doing this for each conversation, a subsequent conversation has a knowledge base (knowledge graph) of non-medical "memories" from which the AI agent can pull to create familiarity rapport with the human patient. The KV cache may be used for subsequent patient conversations with the same patient to enable (i) medical data associated with the patient to be quickly accessed, (ii) non-medical data associated with the patient to be interjected into the conversation to, for example, motivate the patient, and (iii) reduce latency, particular in long, multi-turn conversations.

The systems and techniques may use chunking to avoid AI repetition (also called AI looping). AI repetition refers to the tendency of some AI systems to repeat words, phrases, or even entire sentences, either verbatim or with minor variations, particularly in long, multi-turn conversations (e.g., 60-80 or more turns). To address this, the systems and techniques described herein divide the conversation into chunks. Chunking is the process of breaking down the data (text) associated with conversation into smaller pieces known as "chunks". By dividing the data into smaller pieces, the AI can process the data more effectively, resulting in faster retrieval times, reduced computational load, and more focused analysis. Smaller chunks of data allow the AI model to focus on specific, relevant information, leading to more accurate results and better pattern recognition. Processing smaller chunks of data may reduce the computational load and speed up retrieval time, thereby reducing latency, especially when dealing with large, multi-turn conversations. Effective chunking strategies can maintain the semantic integrity of the text, enabling the AI to understand the context of the information and generate coherent responses. In some cases, a specially trained AI model (LLM) may be used to determine effective chunk boundaries based on the content structure and meaning. In some cases, the chunks may be converted into vector embeddings, e.g., numerical representations of the text, for efficient storage and retrieval in vector databases. One technique to address AI repetition is to determine if a chunk (prior to being output) is similar to a previous chunk (that was output). If the chunk is similar (or identical) to the previous chunk, then the AI model may be instructed to re-compute the output. Another technique to address AI repetition is to send each utterance to two (or more) different AI models and then pick the output that is most diverse from the previous chunk. Yet another technique is to use a router that is designed (configured) to reduce repetition. For example, the router examines each human utterance, determines a predominant particular topic (of the utterance), and sends the utterance to an AI model that specializes in the particular topic.

Multi-Call Memory (MCM)

MCM enables an AI agent to have access to previous conversations between the AI agent and a human (patient). In this way, the AI agent has access to the human's medical data and non-medical data. The term AI agent refers to any instance of an AI agent in an architecture that is capable of providing multiple AI agents to interact with multiple patients. The MCM enables the AI agent to have a conversation with the patient without having to take steps to obtain relevant prior information. In contrast, if the patient is speaking to a human (medical professional), the medical professional would either ask the patient questions or consult the patient's records to obtain relevant prior information. Similarly, if the patient is speaking to an AI agent that does not use MCM, the AI agent may ask the patient questions and/or access the patient's records to obtain relevant prior information. During a conversation with a human, the AI architecture may use dynamic extraction to extract and store particular data from the conversation. The MCM is used to store non-medical memories from individual conversations with the human. The non-medical memories from previous conversation(s) are available to an AI agent in a subsequent conversation to enable the AI agent to speak to the human and create familiarity. Just as a human agent might remember that patient's favorite color is red and that he is an early riser, similarly, the AI agent can access non-medical data, such as a favorite color, favorite food, names of relatives (e.g., children, grandchildren, nieces and nephews), and the like in a manner that shows that the AI agent is knowledgeable about the patient's previous conversations. In this way, MCM enables the AI agents to deliver personalized healthcare-based conversations that show a familiarity with the human patient. For example, the AI agent many mention the name of a grandchild and an activity that the human engages in with the grandchild to motivate the human to exercise regularly, "If you stick with the exercise plan, you can hopefully have many more years of playing soccer with your grandchild, Alex".

Dynamic extraction involves the AI architecture identifying and extracting relevant information from the conversation based on the context and based on user input. Dynamic extraction allows for more flexible and natural interactions, enabling the AI agent to understand user intent and provide tailored responses. The AI architecture may use Natural Language Processing (NLP) to understand the meaning of user input, including identifying keywords and the like and determining the overall intent of the query. By analyzing the conversation history, the AI architecture infers the context of the user's query. Based on the NLP analysis and contextual understanding, the AI architecture extracts the relevant information from the user's input. The extracted information is used to generate a relevant and accurate response, thereby providing a more engaging and satisfying patient experience. In this way, the AI architecture can adapt to a wide range of user inputs and scenarios. After the AI architecture identifies and extracts relevant information, the extracted information is stored in memory in the form of a knowledge graph. The AI agent may access the knowledge graph and bring up portions of the extracted information in an appropriate (natural) way during the conversation. For example, if the patient has indicated they will soon be a grandparent, the AI agent may use this memory to motivate the patient, e.g., "In our last call, you mentioned that you are going to be a grandparent soon. Exercising to get your blood pressure under control will enable you to play with your grandchild as they grow up." In this way, the AI agent invokes the right memory at the right time to help motivate the patient to perform certain actions (e.g., exercise regularly, improve their dietary choices, and so on).

Thus, MCM involves two main steps. First, for individual patients, the AI architecture creates a personalized memory store across multiple cognitive dimensions (motivations, fears, barriers, and the like). For example, the AI agent may make a note that the patient is scared to (i) check their weight in case it has not gone as much as they would like and/or (ii) check their blood pressure as their blood pressure often seems to be higher than normal. Second, the AI agent surfaces the personalized memories at an appropriate point in a subsequent conversation. The AI agent controls which memories are brought into the subsequent conversation to engage the patient in such a way that the patient will share more information that can be used to create new personalized memories that can be used in the future to build rapport, create familiarity, influence patient behavior, and the like. Thus, the AI architecture does something in call N (N>0) that sets up success in future call M (M>N) because the AI architecture knows that there will be multiple conversations with the same patient. In contrast, a conventional AI, such as Chat GPT, doesn't know that there were multiple prior conversations with the same person and so the conventional AI does not distil information from previous conversations into a knowledge graph. MCM knows that the AI agents in AI architecture will likely have multiple conversations and so each conversation is designed to develop a deeper understanding of the patient over time. Each time an AI agent speaks with a patient, the AI architecture builds a knowledgebase about the patient, including for example dietary preferences, lifestyle (e.g., walking, running, playing pickleball, playing tennis, yoga, or the like), daily routine, life story and history, family background, and the like.

The AI models (algorithms) used as the basis for the AI agents are trained on how to use MCM when engaged in a conversation with the patient. For example, if the AI agent determines that the patient has two small children, the AI agent will seamlessly weave this information into the conversation at the appropriate time. In this way, the AI models are (1) trained to create (extract and store) memories and are (2) trained on how to interject the memories into a conversation with the patient.

One advantage of MCM is that interspersing non-medical information into a conversation between an AI agent and a human patient creates a continuous patient journey where when a patient calls, the subsequent conversation makes the patient feel like they are speaking to an old friend, who knows not just their medical history but also personal, non-medical details. A second advantage of MCM is that the AI agent is familiar with both the medical history associated with the patient, enabling the patient to resume a discussion in a subsequent conversation without having to reiterate previously discussed medical information. A third advantage of MCM is that by tokenizing and storing portions of previous conversations in a cache memory, latency is significantly reduced, particularly in longer, multi-turn conversations that are common in a medical context.

As a first example, a conversational artificial intelligence (AI) system includes a large language model (LLM), a conversation analyzer, a knowledge graph constructor, and a knowledge graph applicator. The LLM is configured to execute (engage in) a preceding multi-turn conversation with a user and store the preceding multi-turn conversation in a memory storage device ("memory"). The preceding multi-turn conversation is substantially focused on a target topic, such as a healthcare-related topic. The conversation analyzer has access to the memory and is configured to analyze the preceding multi-turn conversation. Based on the analysis, the conversation analyzer is configured to identify at least some turns in the preceding multi-turn conversation that deviate from the target topic and instead characterize life attributes of the user. The conversational analyzer stores in the memory the at least some turns in the preceding multi-turn conversation that deviate from the target topic and instead characterize the life attributes of the user. The knowledge graph constructor has access to the memory and is configured to build a knowledge graph associated with the user based on the at least some turns in the preceding multi-turn conversation that deviate from the target topic and instead characterize the life attributes of the user. The knowledge graph constructor stores the knowledge graph in the memory. The knowledge graph translates the life attributes of the user into the user's life biography, including life chronology, life preferences, life milestones, life events, or any combination thereof. The knowledge graph applicator has access to the memory and is in communication with the large language model. The knowledge graph application is configured to use parts of the knowledge graph in a subsequent multi-turn conversation with the user. The subsequent multi-turn conversation is also substantially focused on the target topic. The selection of the parts of the knowledge graph is dependent on a current context of the subsequent multi-turn conversation. The use of the parts of the knowledge graph in the subsequent multi-turn conversation may include contextually interspersing portions of the user's life biography into the subsequent multi-turn conversation. The contextual interspersion may include the large language model posing questions to the user based on the user's life biography. The contextual interspersion may include the large language model making assertions to the user based on the user's life biography. The knowledge graph applicator may be a part of the large language model. The knowledge graph applicator may not be a part of the large language model. The knowledge graph may be stored in a tokenized format. For example, the knowledge graph may be stored in the tokenized format in a key-value (KV) cache. The knowledge graph reduces latency of generation of responses by the large language model in the subsequent multi-turn conversation.

As a second example, a conversational artificial intelligence (AI) system includes a large language model (LLM), a conversation analyzer, a knowledge graph constructor, and a knowledge graph applicator. The large language model is configured to execute (engage in) a preceding multi-turn conversation with a user and to store the preceding multi-turn conversation in a memory storage device ("memory"). The preceding multi-turn conversation is substantially focused on a target topic, such as a healthcare-related topic associated with the user. The conversation analyzer has access to the memory and is configured to analyze the preceding multi-turn conversation. Based on the analysis, the conversation analyzer is configured to detect at least some turns in the preceding multi-turn conversation that deviate from the target topic and instead characterize life attributes of the user. The conversation analyzer is configured to store in the memory the at least some turns in the preceding multi-turn conversation that deviate from the target topic and instead characterize the life attributes of the user. The knowledge graph constructor has access to the memory and is configured to build a knowledge graph for the user based on the at least some turns in the preceding multi-turn conversation that deviate from the target topic and instead characterize the life attributes of the user. The knowledge graph constructor stores the knowledge graph in the memory. The knowledge graph applicator has access to the memory and is in communication with the large language model. The knowledge graph applicator is configured to use parts of the knowledge graph in a subsequent multi-turn conversation with the user. The knowledge graph may translate the life attributes of the user into the user's life biography, including life chronology, life preferences, life milestones, and/or life events. Selection of the parts of the knowledge graph may be based on a current context of the subsequent multi-turn conversation. The use of the parts of the knowledge graph in the subsequent multi-turn conversation may include contextually interspersing portions of the user's life biography into the subsequent multi-turn conversation.

As a third example, a pre-acquainted conversational artificial intelligence (AI) agent is configured to express familiarity to and fraternize with a repeat caller, the pre-acquainted conversational AI agent comprising a large language model (LLM) configured to execute a multi-turn conversation with a repeat caller. The multi-turn conversation includes a first class of conversation turns that are substantially focused on a target (e.g., healthcare-related) topic that are contextually interspersed with a second class of conversation turns that are sourced from portions of the repeat caller's life biography. For example, the repeat caller's life biography may be encoded in a knowledge graph. The knowledge graph may be constructed based on one or more prior multi-turn conversations with the repeat caller. The knowledge graph may be constructed based on one or more social media accounts of the repeat caller. The knowledge graph may be constructed based on biographic information of the repeat caller. The tokenized history of the conversation may be stored in a key-value (KV) cache to reduce a latency of the subsequent artificial intelligence response.

As a fourth example, a conversational artificial intelligence (AI) system includes a large language model (LLM) that is configured to execute one or more preceding turns of a multi-turn conversation with a user and is configured to store the preceding turns of the multi-turn conversation in memory. The preceding turns of the multi-turn conversation are substantially focused on a target topic, such as a healthcare-related topic associated with the user. A conversation analyzer that has access to the memory is configured to analyze the preceding turns of the multi-turn conversation. Based on the analysis, the conversation analyzer is configured to detect at least some turns in the preceding turns of the multi-turn conversation that deviate from the target topic and instead characterize life attributes of the user. The conversation analyzer stores in the memory the at least some turns in the preceding turns of the multi-turn conversation that deviate from the target topic and instead characterize the life attributes of the user. A knowledge graph constructor that has access to the memory is configured to build a knowledge graph for the user based on the at least some turns in the preceding turns of the multi-turn conversation that deviate from the target topic and instead characterize the life attributes of the user and store the knowledge graph in the memory. The knowledge graph translates the life attributes of the user into the user's life biography, including life chronology, life preferences, life milestones, and/or life events. A knowledge graph applicator has access to the memory and is in communication with the large language model. The knowledge graph applicator is configured to use parts of the knowledge graph in one or more subsequent turns of the multi-turn conversation with the user, where the subsequent turns of the multi-turn conversation are also substantially focused on the target topic. Selection of the parts of the knowledge graph is dependent on a current context of the subsequent turns of the multi-turn conversation. The use of the parts of the knowledge graph in the subsequent multi-turn conversation may include contextually interspersing portions of the user's life biography into the subsequent multi-turn conversation.

FIG. 1 is a block diagram of a system 100 illustrating large language models (LLMs) to perform specialized healthcare-related functions (e.g., roles), according to some implementations. The system 100 includes a device 102 connected to one or more servers 104 via one or more networks 106. The device 102 may be, for example, a smart phone, or another type of user device associated with a human 108. For example, the human 108 may be a current patient, a past patient, or a potential (future) patient. In some cases, the device 102 may be linked ("paired") with a monitoring device ("monitor") 103, such as a smart watch, a continuous glucose monitor (CGM), or another type of device that is capable of providing biometric readings associated with the human 108 to the device 102.

One or more provider devices 110 may be connected to the network 106. The provider devices 110 may be used by one or more medical professionals 112 (e.g., medical technicians, nurses, nurse practitioners, doctors, and the like) associated with a medical provider.

The server 104 may host multiple AI-based virtual assistants, such as the large language model (LLM) 130 virtual assistants. The virtual assistants LLM 130(1) to 130(6) shown in FIG. 1 each perform a particular healthcare-related role. Six LLM 130 are shown purely for illustration purposes. It should be understood that the number of virtual assistants LLM 130 may vary depending on how the healthcare functions (roles) are divided. The division of the healthcare functions influences the algorithm design, training data, and other details associated with the virtual assistants 130. A different division of the healthcare functions may result in fewer or more than six virtual assistants LLM 130. For illustration purposes, the six functions (roles) include orders 114, intake 116, scheduling 118, pre-op 120, discharge 122, and chronic care 124.

The orders 114 role may include the LLM 130(1) engaging in a conversation 154 with the human 108 to resolve unfilled orders 126. Unfilled orders 126 refers to prescribed medications that the human 108 has not picked up, prescribed medical procedures or follow-up appointments that the human 108 has not scheduled, and so on. The orders 114 role may include the LLM 130(1) entering into a conversation 154 with the human 108 to perform preventative screenings 128, including gathering data relative to Healthcare Effectiveness Data and Information Set (HEDIS) calculations.

The conversation 154 may include audio data 150 output by one of the LLM 130 and one or more utterances 152 from the human 108. The human 108 may speak the utterances 152 into a microphone of the device 102 and the device 102 may send the utterances 152 to the LLM 130 over the network 106. The LLM 130 may provide audio data 150 over the network 106 for playback by the device 102 to the human 108. The conversation 154 may be initiated by the LLM 130 or by the human 108.

The intake 116 role may include the LLM 130(2) engaging in the conversation 154 to perform the role of an intake nurse 132. For example, the conversation 154 may include the LLM 130(2) providing the human 108 with appointment-related information, such as a location and date and time associated with the appointment. The intake 116 role may include the LLM 130(2) engaging in the conversation 154 to perform a Health Records Assessment (HRA), determine a Risk Adjustment Factor (RAF), or the like.

The scheduling 118 role may include the LLM 130(3) engaging in the conversation 154 with the human 108 to perform scheduling and waitlisting related actions. For example, the LLM 130(3) may schedule the human 108 for an appointment and/or waitlist the human 108 for a consultation, surgery, or another type of appointment. The scheduling 118 role may include the LLM 130(3) engaging in the conversation 154 with the human 108 to access a provider directory to select a provider for the human 108. For example, if the human 108 has been asked (e.g., by a primary care physician) to have a consultation with a specialist, then the LLM 130(3) may identify a particular specialist in the provider directory 138 and schedule the human 1084 consultation with the particular specialist.

The pre-op 120 role may include the LLM 130(4) engaging in the conversation 154 and taking on the role of a pre-op nurse 140 to go through a pre-op checklist with the human 108. For example, the pre-op checklist may include various pre-op do's and don'ts, such as what to eat, what not to eat (e.g., avoid solid foods at least 24 hours prior to a colonoscopy, avoid eating 12 hours prior to a blood glucose test, etc.), what medications to take, what medications to avoid taking (e.g., no beta blockers prior to a treadmill stress test), type of clothing to wear (e.g., loose clothing prior to a treadmill stress test), and so on.

The discharge 122 role may include the LLM 130(5) engaging in the conversation 154 to go over a discharge checklist 142. For example, the discharge checklist 142 may include describing what to do and what not do (e.g., don't perform certain action for a particular period of time after certain types of surgery), reviewing medications to take (e.g., take X every day, take Y as needed, and the like), highlighting warning signs (e.g., call medical provider immediately if the human 108 experiences particular symptoms, such as shortness of breath, dizziness, blurry vision, or the like), making follow-up appointments, and the like. The discharge 122 role may include the LLM 130(5) providing information regarding insurance coverage, explanation of benefits (EOB), and other billing-related information (e.g., amount that insurance should cover, amount that the human is responsible for paying, and so on).

The chronic care 124 role may include the LLM 130(6) performing the role of a chronic care nurse when engaging in the conversation 154 with the human 108. For example, the chronic care 124 role may include reviewing medical records and test results, and providing information regarding self-management, such as direct/nutrition suggestions, exercise suggestions, advice on managing prescription regimens, and information regarding monitoring symptoms. The chronic care 124 role may include the LLM 130(6) engaging in the conversation 154 to determine social determinants of health (SDOH), which are the non-medical factors that influence health outcomes. SDOH include the conditions in which people are born, grow, work, live, and age, and the systems shaping the conditions of daily life, such as economic policies, development agendas, social norms, social policies, and political systems.

Thus, a medical provider may deploy AI engines, in the form of a large language model (LLM) or similar AI, to perform specialized health-related tasks. Each AI engine may be designed and trained for a particular purpose, such as screening, intake, scheduling, pre-op, discharge, chronic care, and the like. The advantages of using AI engines include (i) reducing costs compared to using a human, (ii) freeing up humans to perform in-person functions (roles), (iii) performing the health-related tasks at times that are convenient, including outside regular business hours, and (iv) reducing human error when performing the health-related tasks.

Figure 2:
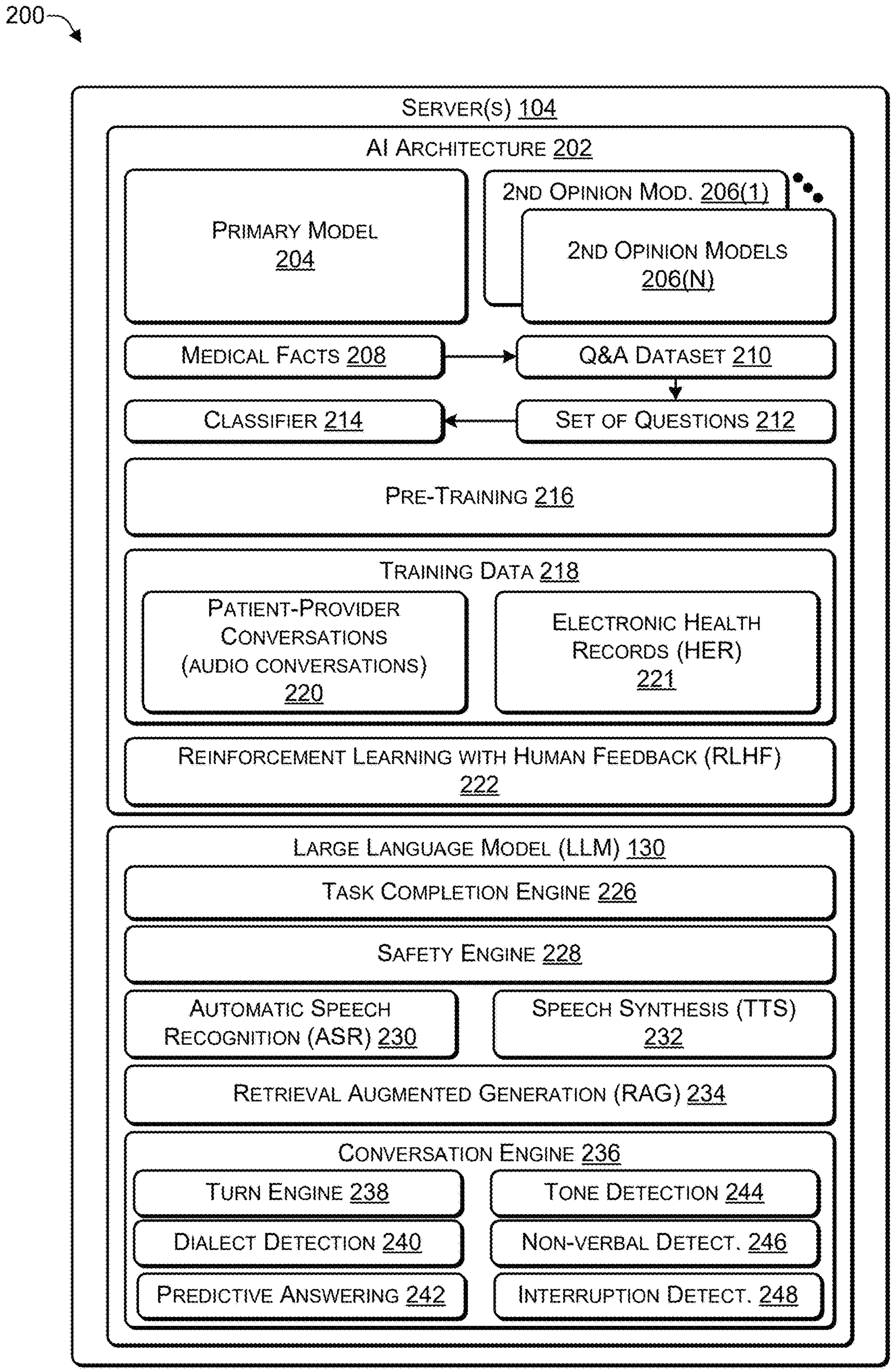
FIG. 2 is a block diagram illustrating an artificial intelligence (AI) architecture, according to some implementations.

FIG. 2 is a block diagram 200 illustrating an artificial intelligence (AI) architecture 202, according to some implementations. The AI architecture 202 may be used to implement one or more of the LLMs (e.g., LLM 130(1), 130(2), 130(3), 130(4), 130(5), and 130(6) of FIG. 1) described herein.

The AI architecture 202 may include a primary model 204 which implements a primary role, such as screening, intake, scheduling, pre-op, discharge, chronic care, or any combination thereof. One or more second opinion models 206(1) to 206(N) (N>0) may be associated with the primary model 204. The second opinion models 206 are AI models, such as LLMs, that are trained to perform a more in-depth analysis than the LLM 130. Based on information extracted from the conversation 154 (of FIG. 1), one of the second opinion models 206 may perform a detailed (e.g., lengthy) analysis while the human 108 is engaged in the conversation 154 with one of the LLM 130. For example, the primary model 204 may have a 50 millisecond (ms) latency while the individual second opinion models 206 may have a 200 ms latency. If the second opinion model 206 determines that particular information provided by the LLM 130 during the conversation 154 can be clarified or expanded upon, then the second opinion model 206 may provide, to the LLM 130, the particular information along with a suggestion regarding how to present the particular information to the human 108. In this way, the primary model tool for and the second opinion models 206 are part of a low-latency conversational artificial intelligence (AI) architecture with a parallelized in-depth analysis feedback loop for healthcare-related applications. The purpose of reducing latency is to prevent the human from hanging up in frustration or due to the human erroneously concluding that the conversation has concluded or the virtual assistant has encountered an error.

A large corpus of medical facts 208 are gathered and converted into a Question & Answer (Q&A) dataset 210. The Q&A dataset 210 may be used to create a set of questions 212. For example, the medical facts 208, such as a description of an illness from a textbook, and converting the description into a Q&A structure, including "What is <illness>?", "What are the symptoms of <illness>?", "How is <illness> treated?", "Who usually gets <illness>?", "Is <illness> common?", and so on. Similarly, tables and other structured data included in the medical facts 208 are converted into a Q&A structure. One or more additional LLMs may be used to determine whether a particular question in the set of questions 212 is relevant. A classifier 214 (e.g., a support vector machine (SVM) or another type of classifier) is used to determine (predict) a distance between individual questions and their corresponding answer to determine if the answer is correct. In pre-training 216, a question is a prompt (e.g., a query presented to the models 204, 206) and the answer is the response predicted by the models 204, 206. The Q&A dataset 210 may be used to fine tune the LLM 130. For example, instruction tuning may be used to further train the LLM 130 on the Q&A dataset 210 (e.g., that is in the form of (instruction, output) pairs), in a supervised fashion.

Training data 218 includes human-provider (e.g., patient-medical professional) conversations 220 in the form of audio data and electronic healthcare records (EHR) 221. By training the LLM 130 using conversation data, the LLM 130 is more suited to engaging in the conversation 154 with the human 108. The AI architecture 202 includes providing the LLM 130 with reinforcement learning with human feedback (RLHF) in which the LLM 130 is trained using a reward function ("reward model") based on human feedback. The reward function provides the LLM 130 with a high reward for good output and a low reward for bad (poor) output. In this way, the LLM 130 is trained to provide the appropriate at each turn in a conversation.

The LLM 130 (representing one of the LLMs 130(1) to 130(6) of FIG. 1) includes a task completion engine 226 that is tasked with completing a checklist during a particular conversation with the human. The task completion engine 226 enables the LLM 130 to complete tasks included in the checklist even while pursuing peripheral matters during the conversation, where such peripheral matters may help to build rapport between the virtual assistant and the human. For example, during the conversation with the human, the human may ask a question, such as a request for clarification of a particular topic ("Can I eat X prior to having the procedure?"). In response, the LLM 130 may provide information to answer the human's question. The LLM may also engage in banter about favorite foods, or the human's experiences with the foods, etc. After the LLM 130 answers the human's question and or engages in banter, the task completion engine 226 causes the LLM 130 to resume addressing items in the checklist. The LLM 130 may include a safety engine 228 to determine a medical accuracy of the information provided by the LLM 130 to the human. The safety engine 228 may determine when to perform a "kick out" and transfer a conversation between a human and an LLM to a medical professional.

The LLM 130 includes an automatic speech recognition module (ASR) 230 to perform speech recognition of the utterances 152 provided by the human 108. The LLM 130 includes a speech synthesis module 232 to perform text-to-speech (TTS) conversion. For example, after the LLM 130 looks up text-based information, the information is provided to the human in the form of speech using the speech synthesis module 232. The ASR 230 may include multiple ASR modules. For example, one or more of the multiple ASR modules may perform background noise reduction. As another example, two or more of the multiple ASR modules may implement different algorithms to recognize different accents, colloquialisms, and the like and the outputs of the multiple ASR modules may be analyzed and reconciled to provide a single ASR output.

The LLM 130 includes a retrieval augmented generation (RAG) module 234. The RAG 234 is an AI framework to retrieve facts from an external knowledge base to provide the LLM 130 accurate and up-to-date information. The RAG 234 grounds the LLM 130 on external sources of knowledge to supplement the LLM 130. Implementing RAG 234 in an LLM-based question answering system enables the LLM 130 to access current, reliable facts, and the access to the sources of the LLM 130, enables output of the LLM 130 to be checked for accuracy. Using RAG, the AI-based virtual assistant described herein can provide accurate answers to a large number of questions that a human could not, such as menu options for a large number of local restaurants, details for a large number of insurance policies, details about a large number of hospital facilities (such as parking information, department locations, etc.).

The LLM 130 includes the conversation engine 236. The conversation engine 236 includes a turn engine 238, dialect detection 240, predictive answering 242, tone detection 244, nonverbal detection 246, and interruption detection 248. The turn engine 238 determines when the human has completed a turn and the LLM 130 has a turn in the conversation. The dialect detection 240 detects a dialect in the utterances of the human and causes the LLM 130 to output audio data having the same (or similar) dialect. For example, the dialect detection 240 may detect the dialect based on a particular word or a particular phrase in the human's utterances. To illustrate, the particular word or the particular phrase may be a vernacular term used in a particular geographic region.

The predictive answering 242 may predict multiple responses that the human may utter based on what the LLM 130 previously provided to the human. For example, the LLM 130 may provide a particular output (audio data) during the LLM's turn and then listen to the human during the human's turn. The predictive answering 242 may predict (i) possible human responses and (ii) corresponding answers based at least in part on the particular output provided during the LLM's turn. After the human has completed providing utterances in the human's turn, the LLM 130 may determine which of the predicted human responses the human provided and select a corresponding predicted answer. In this way, the predictive answering 242 is able to reduce the latency when providing a response after the human's turn.

The tone detection 244 is able to detect that the tone and changes to the tone in the human's utterances during the conversation. For example, the tone detection 244 may be able to detect a tone of the human's utterances, correlate the tone with a particular mood, and adjust the audio data output by the LLM 130 accordingly. To illustrate, the tone of the human's utterances may be determined based on a pitch of the utterances, a volume of the utterances, a particular word in the utterances, a particular phrase in the utterances, or any combination thereof. If a particular tone is detected, such as that of anger or frustration, then the LLM 130 may adjust the audio data output accordingly, including changing the pitch of the audio data, changing a volume of the audio data, inserting a particular word or a particular phrase in the audio data, or any combination thereof. In some cases, if the tone of the human is regressing instead of progressing (e.g., the human has become more angry or more frustrated in a subsequent turn), then the LLM 130 may offer to transfer ("kick out") the conversation to a human. The non-verbal detection 246 may detect the human coughing, sneezing, sighing, crying, or providing another nonverbal audio cue. Detecting one of the nonverbal audio cues may cause the LLM 130 ask additional (e.g., follow-up) questions, such as "How long have you had that cough?" (in response to detecting a cough), "How long have you had nasal congestion?" (in response to detecting a sneeze or sniffling), "Are you feeling okay?" (in response to detecting a loud sigh or crying), or the like. The interruption detection 248 may detect when the human is attempting to interrupt the LLM 130 and cause the LLM 132 yield its turn and provide the human with a turn to enable the human to interject additional utterances into the conversation.

Thus, an AI architecture may include a primary model and one or more second opinion models to provide a low-latency conversational AI with a parallelized in-depth analysis and feedback loop in which the primary model engages in a low latency conversation with the human while the second opinion model gathers additional data and provides feedback (e.g., clarification or expansion of something that the primary model said to the human). Unlike conventional conversational AI's, the training data includes human provider audio-based conversations in addition to text-based training data. The LLM is trained using RLHF to provide improved conversational abilities to the LLM. The LLM may use a task completion engine to avoid missing any items on a checklist of items to be covered with the human. The conversation engine used by the LLM may include a turn engine to determine when the human's turn has ended and the LLM's turn begins, dialect detection to understand and respond to the human in a local dialect, predictive answering to reduce latency by predicting possible answers while the human is talking, tone detection to detect emotional cues (e.g., based on a change in pitch, a change in volume, or the like) in the human's voice, non-verbal detection (e.g., coughing, sneezing, crying, or the like), and interruption detection to detect when the human is attempting to interrupt the LLM. In this way, the LLM is able to provide an engage in a conversation with a human in a manner similar to a human. The purpose of reducing latency is to prevent the human from hanging up in frustration or due to the human erroneously concluding that the conversation has concluded or the virtual assistant has encountered an error.

Figure 3:
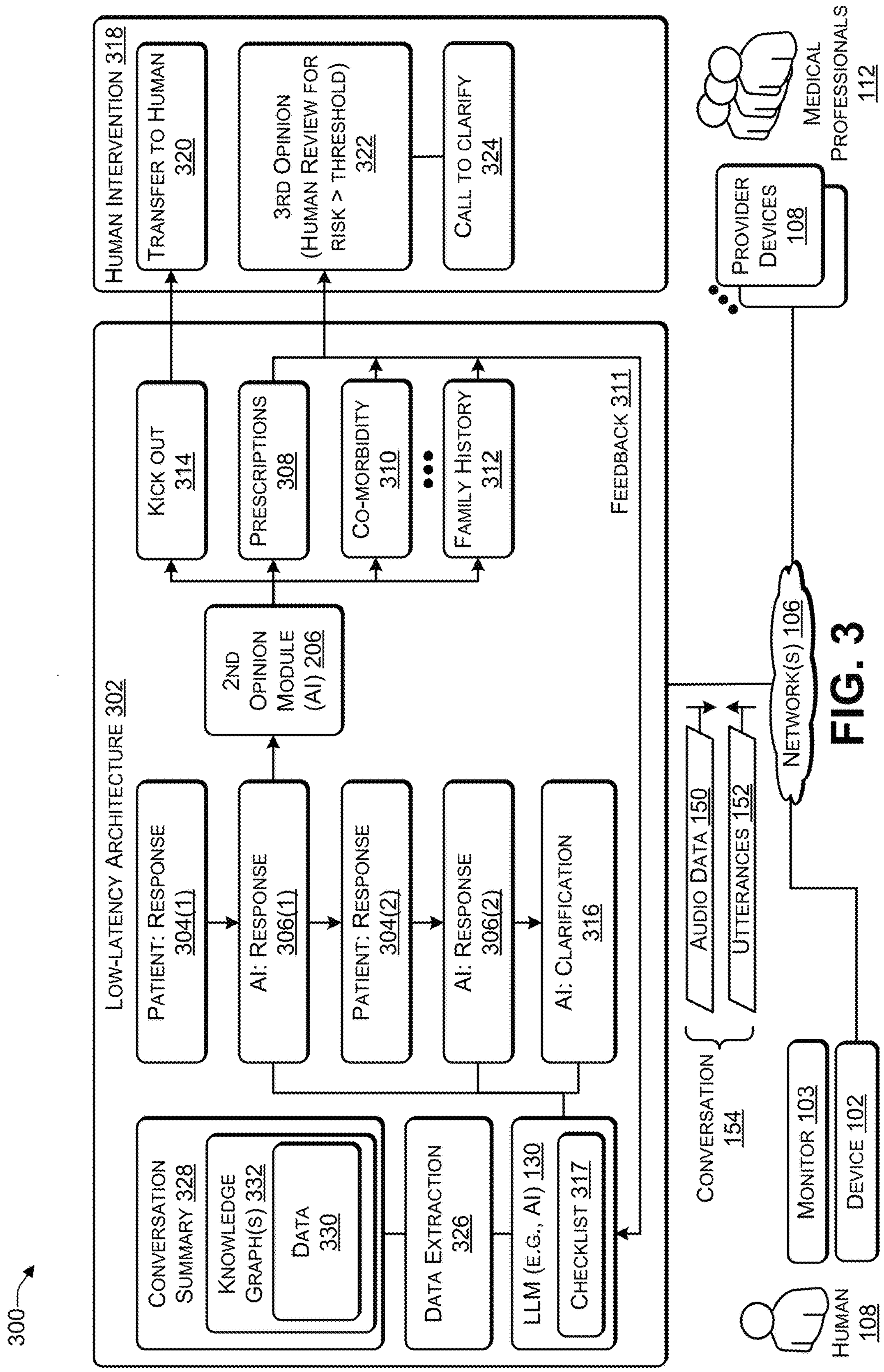
FIG. 3 is a block diagram of a system that includes a low-latency conversational artificial intelligence (AI) architecture with a parallelized in-depth analysis and feedback loop, according to some implementations.

FIG. 3 is a block diagram of a system 300 that includes a low-latency conversational artificial intelligence (AI) architecture with a parallelized in-depth analysis and feedback loop, according to some implementations. The system 300 includes a low latency architecture 302 in which the LLM 130 receives a (first) response 304(1) from the human 108. The LLM 130 may engage in the conversation 154 with the human 108 based on a checklist 317 that identifies tasks that the LLM 130 is to complete during the conversation 154. The LLM 130 provides a (first) response 306(1) to the human 108. The LLM 130 receives a (second) response 304(2) from the human 108 and provides a (second) response 306(2) to the human 108. While the LLM 130 is engaged in the conversation 154 with the human 108, the second opinion module 206 may, in parallel (substantially at the same time), do a lengthier "deep dive" by performing research into the human response 304(1) and the AI response 306(1). For example, the research may include prescriptions 308, co-morbidity 310, family history 312 and the like. The prescriptions 308 may include determining whether the human 108 is being prescribed prescriptions appropriate to the human's conditions, determining whether the human 108 is being prescribed the correct dosages of the prescriptions, determining whether the prescribed prescriptions have any undesirable interactions or contraindications, and other prescription related information. The prescriptions 308 may include a dosage engine that is invoked every time there is mention of a drug, dosage, or both. The co-morbidity 310 may include determining whether the human 108 has two or more medical conditions that may be related to an underlying cause or that have an undesirable interaction. The family history 312 may include determining whether the human's parents, siblings, or other relatives have a history of medical conditions similar to that of the human 108.

Based on determining the research into the prescriptions 308, the co-morbidity 310, and the family history 312, the second opinion module 206 may determine whether the AI response 306(1) was appropriate or whether the AI response 306(1) may be clarified. If the second opinion module 206 determines that the response 306(1) is appropriate, the second opinion module 206 does not take further action. If the second opinion module 206 determines that the response 306(1) may be clarified, then the second opinion module 206 may provide feedback 311 to the LLM 130, causing the LLM 130 to provide a clarification 316. For example, the human response 304(1) may be "Can I have soup?" and the AI response 306(1) may be "yes, you can have soup.". The clarification 316 may be "I previously said you could have soup. I noticed that either you or at least one of your family members have high blood pressure, so please check the sodium content of any pre-packaged soups and avoid soups with high sodium." In this example, "you . . . have high blood pressure" was determined by checking co-morbidity 310 and "at least one of your family members have high blood pressure" was determined by checking family history 312. As another example, the clarification 316 may be "I noticed that you are currently taking <1st prescription> in the morning. Instead of taking <2nd prescription> in the morning as I previously suggested, I suggest taking <2nd prescription> in the evening, around 12 hours after taking <1st prescription>." In this example, by checking the prescription 308, the second opinion module 206 may determine that the patient is taking the 1st prescription and that the 2nd prescription (mentioned in the AI response 306(1)) is not to be taken at the same time as the 1st prescription and instruct the LLM 130 to clarify when to take the 2nd prescription. As a further example, the clarification 316 may be "I noticed that your potassium was high in your most recent blood work. While I had previously suggested eating more avocados (for the oil), I suggest not having more than one avocado a week to avoid raising your potassium further, as avocados are high in potassium". In this example, by checking the co-morbidity 310 that includes test results (such as the results of a blood workup, e.g., comprehensive metabolic panel), the second opinion module 206 may determine that the patient has a high potassium level and that avocados are high in potassium and clarify how many avocados the human can have in a particular time frame.

In some cases, the second opinion module 206 may determine that providing the clarification 316 is insufficient and that the conversation 154 would benefit from human intervention 318. In such cases, the second opinion module 206 may use a kick out 314 engine to determine to transfer the conversation 154 to the medical professional 320 (e.g., human nurse or doctor). In addition, if the second opinion module 206 determines that a risk to the human 108 is greater than a predetermined threshold, then the second opinion module 206 may initiate a request for a third opinion 322 in which a human (e.g., a doctor, such as a specialist) reviews the human's case and takes appropriate action (e.g., provides a call (to the human 108) to clarify 324 the situation). The kick out engine will be invoked for qualitative statements that suggest symptoms that require further evaluation.

While the LLM 130 is engaged in the conversation 154 (e.g., the responses 304, 306), one or more background processes may perform data extraction 326 to extract data 330 (e.g., pertinent information, such as facts) to create a conversation summary 328 which is stored in the form of a knowledge graph 332 (or another type of data structure). The conversation summary 328 and the data 330 may enable the LLM 130 to quickly access earlier information in a lengthy conversation. With medical-related AI, conversations may be lengthy and involve many turns (e.g., 50 to 100 turns is common and the conversation may, in some cases, include 200 or even 300 turns). In such a lengthy conversations, the human 108 may reference previously provided information ("referenced information") in a current response. If the referenced information was provided early in the conversation, a conventional virtual assistant may have "forgotten" the referenced information and thus provide responses that are frustrating to the human. Alternatively, a conventional virtual assistant may have to scan through a transcript of the conversation to determine the referenced information. Such a scan may cause a lengthy delay and introduce latency into the conversation 154. By performing data extraction 326 and creating the conversation summary 328 and maintaining the knowledge graph 332 storing the data 330, the LLM 130 is able to quickly access the information (data 330) referenced by the human, thereby reducing latency. The purpose of reducing latency is to provide a natural sounding conversation and prevent the human from hanging up (i) in frustration or (ii) due to the human erroneously concluding that the conversation has concluded or the virtual assistant has encountered an error.

Thus, a low latency architecture for a conversational AI includes an AI, such as an LLM, engaged in a conversation with the human. While the AI is engaged in the conversation with the human, a second opinion module does a more in-depth analysis of information provided by the human. If the second opinion module determines that a response provided by the conversational AI is to be clarified, the second opinion module provides feedback that the conversational AI uses to provide a clarification to the human during the conversation. By parallelizing the second opinion module with the conversational AI, latency is reduced, thereby making the conversation more natural. In addition, while the conversational AI is engaged in the conversation with the human, a data extraction module (in parallel)

extracts facts from each human response and creates a conversation summary in the form a data structure that can be quickly searched, such as a knowledge graph. The conversational AI can quickly access the conversation summary to look up information previously provided by the human that the human is referencing in a current turn in the conversation. The access to the conversation summary enables the conversational AI to reduce latency because the conversation AI is not pausing the conversation to perform a search of a transcript of the conversation.

Figure 4:
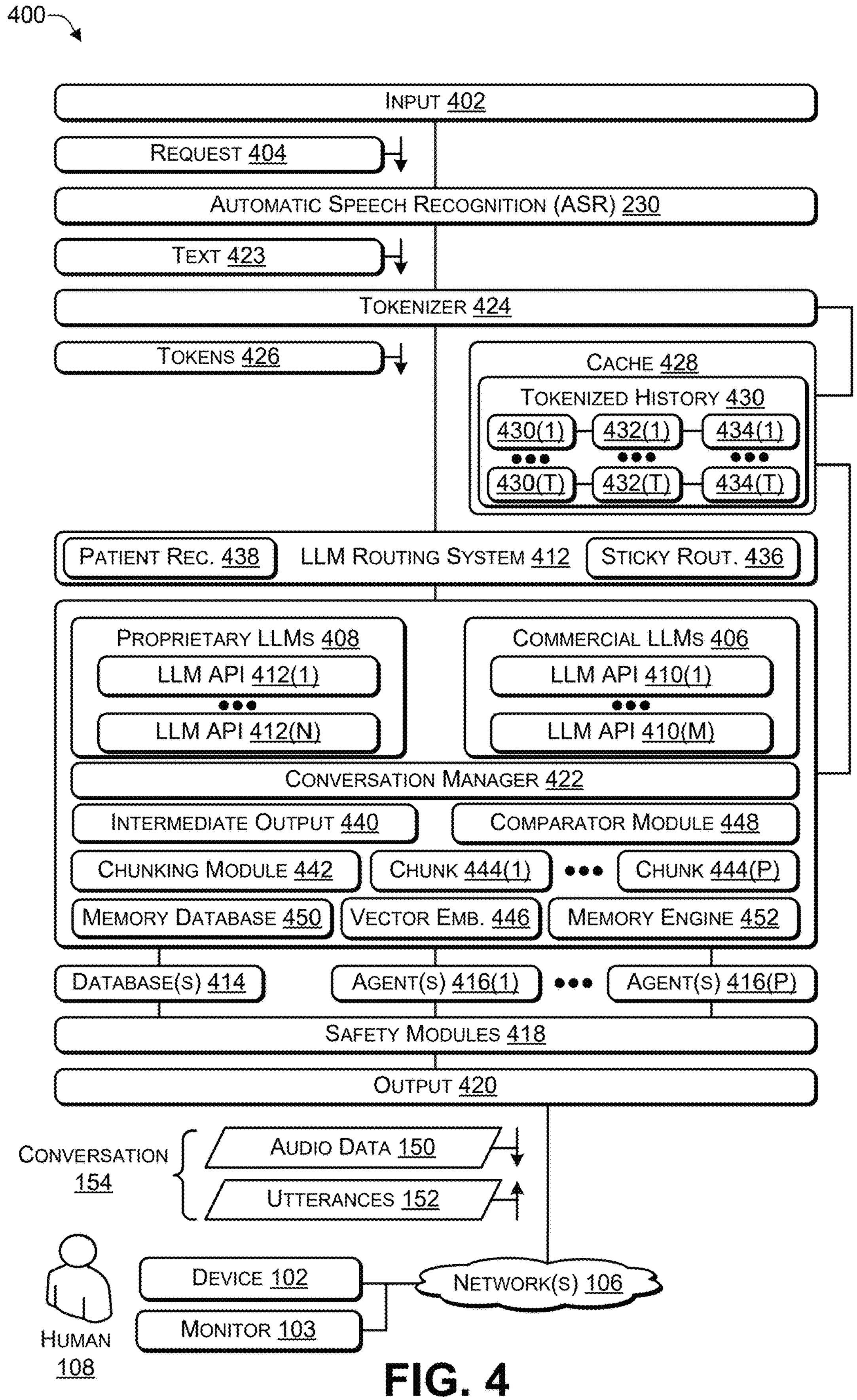
FIG. 4 is a block diagram of a system that includes a cache to store a tokenized history of a conversation, according to some implementations.

FIG. 4 is a block diagram of system 400 that includes an LLM routing system, according to some implementations. FIG. 4 illustrates an example conversational AI system, according to some implementations. In some examples, the system 400 can be implemented using one or more servers that collectively implement processes for enabling examples as described. In variations, system 100 can be implemented in part using client or user devices, such that an architecture described with an example of FIG. 1 is distributed. Further, with reference to FIG. 1, the system illustrates an LLM-based architecture to process system input and generate output. The system 100 can be implemented for a variety of applications, such as, for example, medical-related applications, and applications for implementing bedside manners.

In some examples, the input of system 400 can be in multiple modalities, such as text, speech, images, audio and video. The system 400 can accept input from a variety of sources, such as users, sensors, and other systems. Further, the system 400 may use a commercial (off-the-shelf) large language model (LLM) 406 (that has been trained with specific data) to process the system input 402. The LLM 406 can be used to understand the input 402, generate text, translate languages, and answer questions. In some examples, the system 400 may use a proprietary LLM 408 instead of or in addition to the commercial LLM 406. The proprietary LLM 408 can be trained on a specific dataset to improve its performance for a particular task.

In some examples, the system 400 can use an LLM application programming interface (API) to access the LLMs 406, 408. For example, LLM APIs 410(1) to 410(M) (M>0) may be used to access commercial LLMs 406. The LLM APIs 412(1) to 412(N) (N>0) may be used to access the proprietary LLMs 408. The LLM APIs 410, 412 can be used to send requests to the LLMs 406, 408 and receive responses from the LLMs 406, 408. The system 400 can use a proprietary LLM routing system 412 to route requests, such as a representative request 404 to the appropriate LLMs 406, 408. The LLM routing system 412 can be used to improve the performance and efficiency of the system 400 by routing requests to the LLMs 406, 408 that are best suited for the task associated with the request 404.

Further, in examples, the system 400 can use one or more databases 414 to store data. The data can be stored in a variety of formats, such as text, images, and video. The system 400 can use a variety of tools and agents 416(1) to 416(P) (P>0) to perform tasks. The tools and agents 416 can be used to generate text, translate languages, answer questions, and perform other tasks. The system 400 can use safety modules 418 to prevent the system from performing unsafe actions. The safety modules 418 can be used to prevent the system 400 from generating text that is harmful, offensive, illegal, or the like and that complies with various medical standards.

The system 400 can generate output 420 in multiple modalities, such as text, speech, images, and video. The output 420 can be sent to a variety of destinations, such as users, sensors, and other systems. The output of the system 400 is combined to provide appropriate vocal utterances to the human. In examples, system 400 implements voice conversations in a healthcare setting or environment. The system 400 can incorporate multiple large language models (LLMs) 406, 408 and a conversation manager 422 to facilitate natural language interactions between humans and healthcare providers. The system 400 includes a front-end interface that is accessible via voice assistants or mobile applications. When a human initiates a conversation, the system uses automatic speech recognition (ASR) technology to transcribe the spoken input and convert it into text. The text is then processed by the conversation manager 422, which uses advanced natural language understanding (NLU) techniques to identify the intent of the human's request and route it to the appropriate LLM.

The LLMs 406, 408 may be fine-tuned for specific healthcare domains, such as cardiology, radiology, or dermatology, to ensure high accuracy and relevance of the responses. Each LLM 406, 408 is trained on a large corpus of healthcare data, including electronic health records, medical literature, and human feedback, to provide a comprehensive knowledge base for the conversation. The system 400 also includes a set of targeted sub-domain adapter models for medical coding, compliance, pharmacist, nurse practitioner, and dentist. Each domain-specific module has a distinct set of self-auditing correction mechanisms and utilizes separate knowledge retrieval databases.

The conversation manager 422 coordinates the flow of the conversation between an LLM and a human by selecting the appropriate LLM based on the human's request and ensuring a coherent and engaging dialogue. The system 400 incorporates conversational strategies, such as open-ended questions, feedback loops, and active listening techniques, to maintain human engagement and satisfaction. The system 400 implements processes and functionality to ensure that the LLM is factually accurate during conversations with humans to build trust, credibility, and reduce anxiety and stress for humans. To ensure human safety and privacy, the system 400 employs several security and compliance measures. All data can be encrypted and stored securely, and access to the system is restricted to authorized healthcare providers and staff. The system 400 adheres to relevant healthcare regulations, such as the Health Insurance Portability and Accountability Act (HIPAA) and the General Data Protection Regulation (GDPR).

Among other advantages, the system 400 offers a valuable solution for natural language interactions for healthcare-related functions. By incorporating multiple LLMs 406, 408 and a conversation manager 422, the system 400 enables accurate and engaging conversations between humans and LLMs od healthcare providers, leading to improved healthcare outcomes and human satisfaction.

In cases where humans exhibit mild cognitive impairment, the system 400 provides for the LLMs 406, 408 to employ additional adaptive techniques, such as simplified language, visual aids or diagrams, repeating and/or summarizing information, and providing reminders to aid comprehension and retention. The system 400 adapts to the human's level of medical understanding, using appropriate language for effective communication. A proprietary conversational benchmark testing suite to assess the system's ability to communicate effectively and agreeably.

The system 400 implements multiple techniques to reduce latency, such as by using cached conversational elements and parallel layered processing of semantic information. The system 400 performs tone detection to identify mood information and self-modulation to respond appropriately. The system 400 can implement one or more processes to manage dialog by keeping track of existing human information from the database along with new information gathered during the course of the conversation and purposefully accomplishing particular conversational objectives (set an appointment, confirm a prescription is being taken, explain a medical bill, etc.).

The system 400 can implement one or more processes to embed user queries in a high dimensional space, classifying input within several categorical domains, in order to modify and direct it to a matched internal model as part of a pre-processing pipeline. Further, the system 400 can also develop, train, implement or otherwise use a set of safety-focused language models that function to audit the output of the core models for accuracy and agreement with scientific literature and clinical best-practices. Additionally, the system 400 can implement one or more processes to combine domain specific and general retrieval corpuses to improve performance in targeted domains (e.g., medical coding) without sacrificing performance.

Tokenization

In some cases, the input 402 may be converted into text 423 by the ASR 203. Note that for multi-modal models, audio is directly converted into tokens. The text 423 may be divided by a tokenizer 424 into smaller portions, referred to as tokens 426. For example, the tokenizer 424 may use one or more of (1) delimiter-based tokenization, (2) dictionary-based tokenization, (3) sub-word tokenization, (4) byte pair encoding (BPE) tokenization, or any combination thereof. Delimiter-based tokenization involves splitting the text 423 into words based on a delimiter, such as a space. For example, "I am John" may be split into 3 tokens: "I", "am", and "John". Dictionary-based tokenization involves dividing the input 402 into tokens based on a predefined dictionary, with words matching entries in the dictionary treated as tokens. For example, "See John run" may be tokenized as "See", "John", and "run" based on the dictionary. Sub-word tokenization includes dividing words into smaller sub-word components, such as prefix, stem, suffix, and the like, to create tokens. For example, "learning" may be split into the stem "learn" and the suffix "ing". Byte pair encoding (BPE) tokenization includes merging words into tokens based on statistical frequencies in which high-frequency word combinations are combined into a single token. For example, a training corpus may be analyzed to identify the most frequent consecutive pairs of characters or tokens and the most frequent pairs may be merged to create a new token. For example, "myocardial infarction" may be merged to create a new token.

The tokenizer 424 is an AI model that converts the input into the tokens 426. For example, short words may be represented with a single token, while longer words may be split into two or more tokens. For example, the word darkness may be split into two tokens, "dark" and "ness," with each token having a corresponding numerical representation, such as, for example, 217 and 655, respectively. The opposite word, brightness, may similarly be split into "bright" and "ness," with corresponding numerical representations, 491 and 655, respectively. In this example, the shared numerical value associated with "ness" helps the tokenizer 424 (AI model) understand that the words have something in common. In some cases, the tokenizer 424 may assign different numerical representations for the same word based on the context.

The system 400 may use sticky routing 436 to avoid AI repetition (also called AI looping). AI repetition refers to the tendency of some AI systems to repeat words, phrases, or even entire sentences, either verbatim or with minor variations. This can be an issue particularly in long, multi-turn conversations (e.g., 60 to 80 or more turns). To address this, the system 400 may take the conversation (e.g., intermediate output 440 from the LLMs 406, 408 and input 402) and divide the conversation, using a chunking module 442, into chunks 444(1) to 444(T) (T>0). The chunking module 442 breaks down the text 423 and the intermediate output 440 of the conversation 154 into smaller pieces known as chunks 444. By dividing the data into smaller pieces, the LLMs 406, 408 can process the data more effectively, resulting in faster retrieval times, reduced computational load, and more focused analysis. Smaller chunks of data allow the LLMs 406, 408 to focus on specific, relevant information, leading to more accurate results and better pattern recognition. Processing smaller chunks of data may reduce the computational load and speed up retrieval time, thereby reducing latency, especially when dealing with large, multi-turn conversations. Effective chunking strategies maintain the semantic integrity of the text, enabling the LLMs 406, 408 to understand the context of the information and to generate coherent responses. Chunking strategies may include one or more of (i) fixed-size chunking that includes dividing text into chunks of a predetermined size, (ii) semantic chunking that includes dividing text based on semantic meaning and context, to split sentences, separate paragraphs, and the like, or (iii) any combination thereof. In some cases, the chunking module 442 may be a specially trained AI model (LLM) that determines effective chunk boundaries based on the content structure and meaning. In some cases, the chunks 444 may be converted into vector embeddings 446 that are numerical representations of the text, for efficient storage and retrieval in vector databases.

One technique to address AI repetition is to use a comparator module 448 to determine if a subsequent chunk 444 (prior to being output) is similar to a previous one of the chunks 444 (that was previously output). If the subsequent chunk 444 is similar (or identical) to the previous one of the chunks 444, then the LLMs 406, 408 may be instructed to re-compute the intermediate output 440. Another technique to address AI repetition is to send each utterance (input 402) to two (or more) different AI models (of the LLMs 406, 408) and then pick the output that is most diverse from the previous chunk. Yet another technique is to configure the LLM routing system 412 to reduce repetition. For example, the LLM routing system 412 may examine each human utterance (input 402), determine a predominant particular topic (of the utterance), and send the utterance to an AI model (of the LLMs 406, 408) that specializes in the particular topic.

The system 400 may include components to implement multi-call memory (MCM), including a memory database 450 and a memory engine 452. The multi-call memory is described in more detail in FIG. 5.

Figure 5:
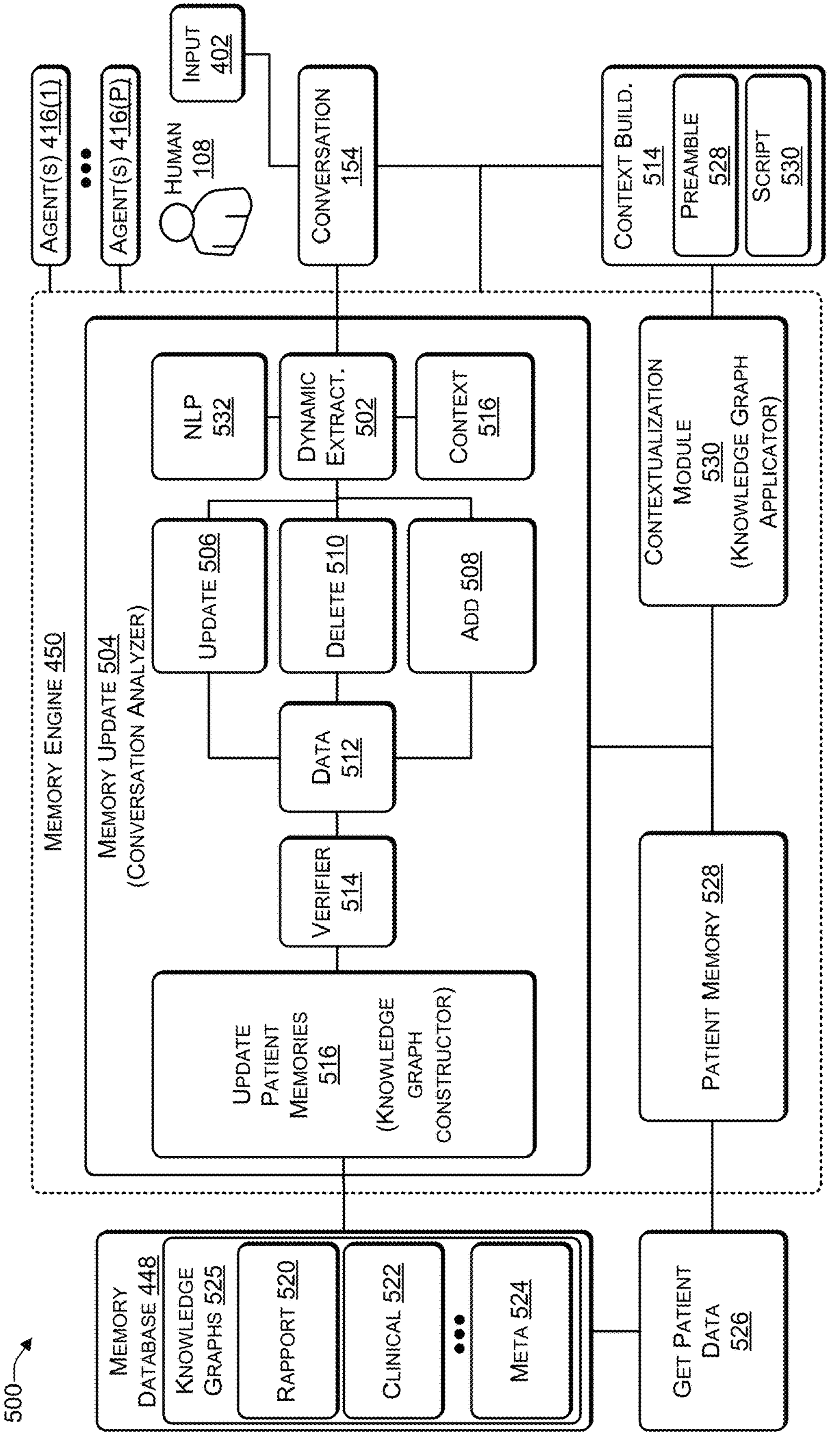
FIG. 5 is a block diagram of a system that includes multi-call memory, according to some implementations.

FIG. 5 is a block diagram of a system 500 that includes multi-call memory (MCM), according to some implementations. MCM enables the AI agents 416(1) to 416(P) to access medical data and non-medical data extracted from previous conversations between the AI agents 416 and the human (patient). The MCM includes the memory database 448 and the memory engine 450. The MCM enables AI agents 416 to reduces latency because the AI agents 416 are able to quickly access data from prior conversations. The MCM enables the AI agents 416 to have a conversation with the human 108 without having to obtain relevant prior information. In contrast, if the human 108 was speaking to a medical professional, the medical professional would either ask the human 108 questions or consult the patient's records to obtain relevant prior information. Similarly, if the human 108 is conversing with a conventional AI agent (e.g., Chat GPT or the like) that does not use MCM, the AI agent may ask the patient questions and/or spend time accessing the patient's records to obtain relevant prior information. In addition, the MCM enables the AI agents 416 to identify and interject relevant non-medical information into the conversation 154 to help build rapport. The MCM creates a personalized memory store across all cognitive dimensions (motivations, fears, barriers). For example, the MCM may store that the human is afraid to check their weight in case it has not gone down or afraid to check their blood pressure as it always shows it is high. The MCM enables the AI agents 416 to surface the personalized memories at the appropriate time during the conversation 154. The AI agents 416 control what memories are brought into the conversation 154 and when they are brought in. This helps the AI agents 416 to engage with the human 108 in a way that the human 108 will share more information that can be used in the future. The personalized memories may also be surfaced to influence patient behavior. Thus, an AI agent may do something in call N that sets up success in call M (M>N) because the AI agent knows that there are likely going to be multiple conversations (not just the current conversation).

The human 108 (patient) provides input 402 that is part of the conversation 154. Dynamic extraction 502 may use natural language processing (NLP) 532 and a context 516 (of the conversation) to extract data 514. The context 516 is dynamically updated such that when the input 402 is received, previous input from the human 108 has been incorporated into the context 516. The operations performed with the data 514 may include update 506 (modify previously stored data in the memory database 448), delete 510 (remove previously stored data from the memory database 448 that has been determined to be semantically false or irrelevant), and add 508 (add data to the memory database 448). The data 512 may be verified by a verifier module 514 before being sent to an update patient memories module 516 that updates the memory database 448. The verifier module 514 determines whether the data 512 is a memory that should be stored in the memory database 448.

The data 512 may be classified into a particular category, such as, for example, a memory used to establish rapport 520, a memory associated with clinical data 522, a memory associated with meta data 524, and the like. These categories are merely examples and other categories may be used instead of or in addition to the ones shown in FIG. 5. The data 512 may be stored in one or more knowledge graphs 525 to enable fast access to relevant information.

During the conversation 154, get patient data 526 may extract a patient memory 528 from the memory database 448. A contextualization module 530 may determine a context where surfacing the patient memory 528 might be appropriate. A context builder 514 may create a preamble 528 and create a script 530 to be used when the patient memory 528 is surfaced.

During the conversation 154 with the human 108, the system 500 may use dynamic extraction 502 to extract and store particular data from the conversation that is predicted to be relevant to future conversations, including both medical data and non-medical data. For example, the particular data may include symptoms that the human 108 is experiencing, medications that the human 108 is taking, major life events, family dynamics, and so on. In this way, even if there is a long history of conversations between the AI agents 416 and the human 108, the AI agents 416 are able to access data extracted from the previous conversations to "get up to speed" and start conversing with the human 108 in a manner that shows that the AI agent 416 is knowledgeable about the patient's previous conversations. In this way, MCM enables the AI agents 416 to deliver personalized healthcare-based conversations.

Dynamic extraction 502 includes identifying and extracting relevant information from the conversation 154 based on a context 516 and based on user input 402. Dynamic extraction 502 allows for more flexible and natural interactions, enabling the AI agents 416 to understand user intent and provide tailored responses. The system 500 may use Natural Language Processing (NLP) 532 to understand the meaning of user input 402, including identifying keywords and the like and determining an overall intent of the input 402. By analyzing the conversation history, the AI agents 416 are able to infer a context of the user's input 402. Based on the NLP 532 analysis and contextual understanding, the AI agents 416 extract relevant information from the user's input 402. The extracted information is used by the agents 416 to generate a relevant and accurate response, thereby providing a more engaging and satisfying patient experience. In this way, the systems and techniques described herein can adapt to a wide range of user inputs and scenarios. After the system identifies and extracts relevant information, the extracted information is stored in a memory database 448.

The AI agent 416 may bring up portions of the extracted information from the memory database 448 in an appropriate (natural) way during the conversation 154. For example, if the human 108 has indicated they will soon be a grandparent, the AI agent 416 may use this memory to motivate the patient, e.g., "You mentioned that you are going to be a grandparent soon. Exercising to get your blood pressure under control will enable you to play with your grandchild as they grow up." In this way, the AI agent 416 invokes the right memory at the right time to help motivate the patient to perform certain actions (e.g., exercise regularly, improve their dietary choices, and so on).

Thus, MCM involves two main steps. First, for individual patients, the system creates a personalized memory in the memory database 448 multiple cognitive dimensions (motivations, fears, barriers, and the like). For example, the AI agent 416 may make a note that the human 108 is scared to (i) check their weight in case it has not gone as much as they would like and/or (ii) check their blood pressure as their blood pressure often seems to be higher than normal. Second, the AI agent 416 surfaces the personalized memories from the memory database 448 at an appropriate point in the conversation 154. The AI agent 416 controls which memories are brought into the conversation 154 to engage the human 108 in such a way that the human 108 will share more information that can be used to create new personalized memories that can be used in the future to influence patient behavior. Thus, the system does something in call X (X>0) that sets up success in future call Y (Y>X) because the system knows that there will be multiple conversations with the same human 108 (patient). In contrast, a conventional AI, such as Chat GPT, doesn't understand that they may have multiple conversations with the same human. In contrast, the system knows that the AI agents 416 will likely have multiple conversations with the same human 108 and so each conversation is designed to develop a deeper understanding of the human 108 over time. Each time an AI agent 416 speaks with the human 108, the system builds a knowledgebase (in the memory database 448) about the human 108, including for example dietary preferences, lifestyle (e.g., walking, running, playing pickleball, playing tennis, yoga, or the like), daily routine, life story and history, family background, and the like.

The AI models (algorithms) used as the basis for the AI agents 416 are trained on how to use the MCM when engaged in a conversation with a patient. For example, if the AI agent 416 determines that the patient has two small children, the AI agent may seamlessly weave this information into the conversation at the appropriate time. In this way, the AI models are (1) trained to create (extract and store) memories and are (2) trained on how to interject the memories into a conversation with the patient.

Figure 6:
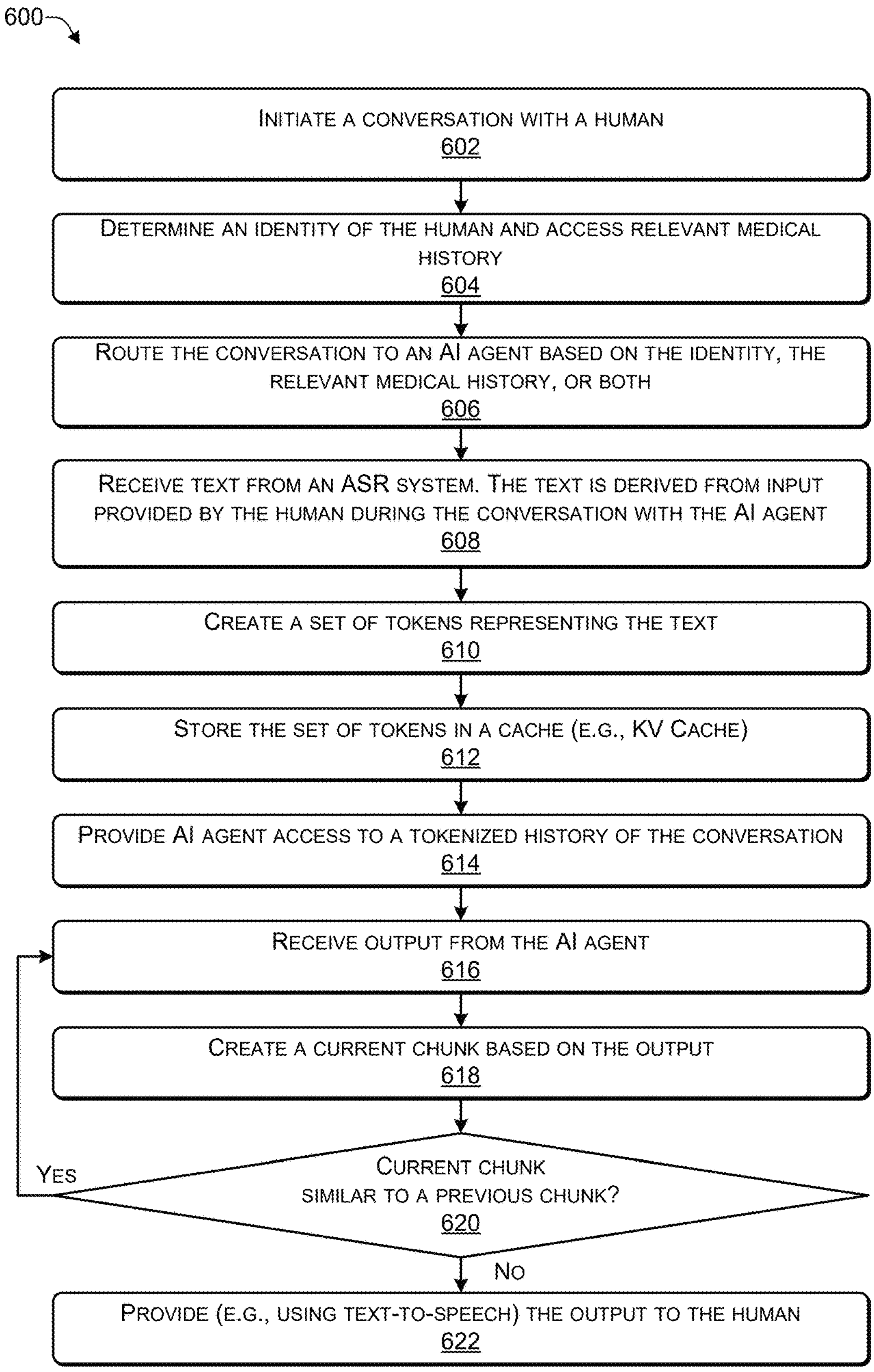
FIG. 6 is a flowchart of a process that includes providing a tokenized history of a conversation to an AI agent, according to some implementations.
Figure 7:
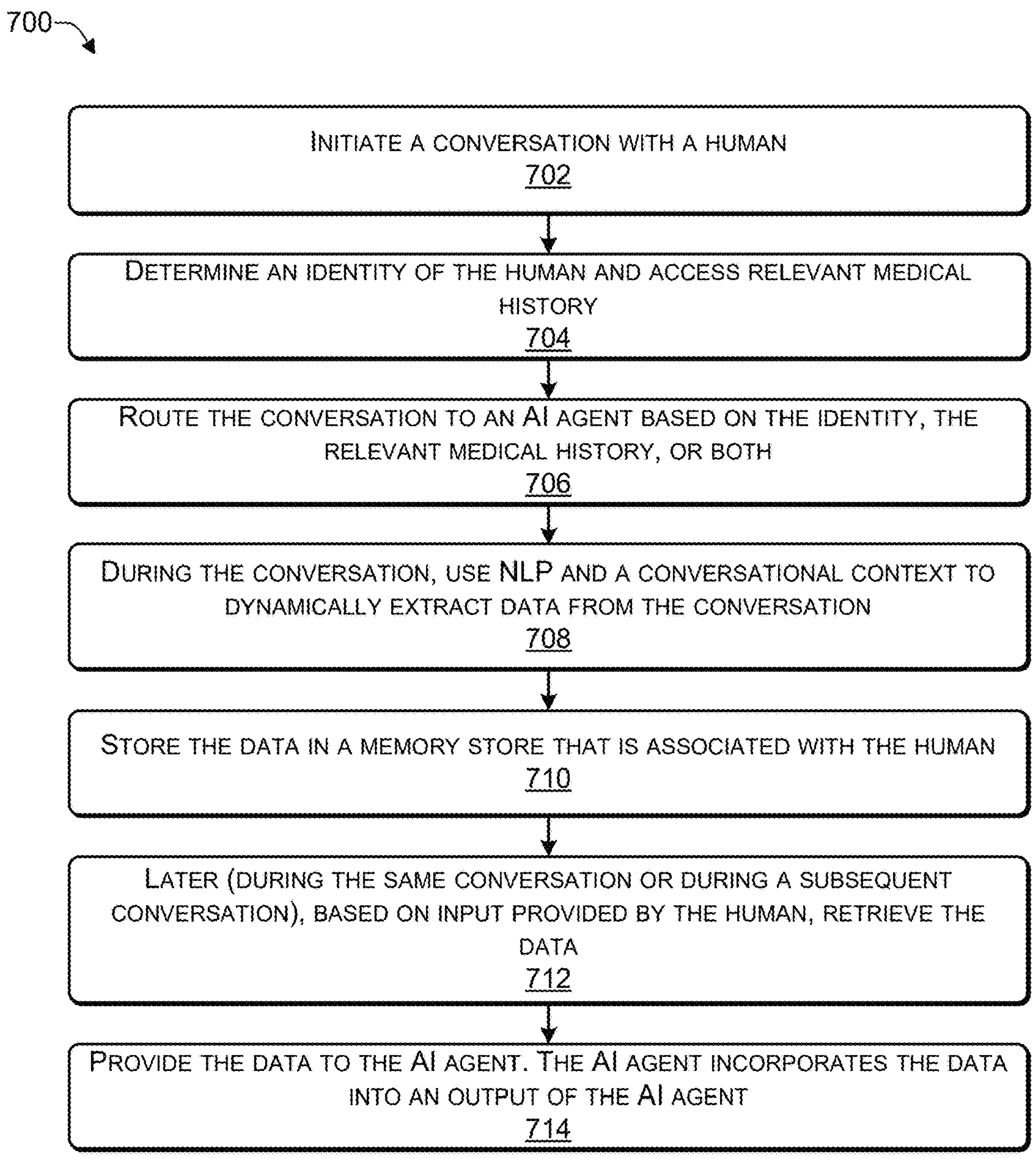
FIG. 7 is a flowchart of a process that stores data extracted from a conversation and later surfaces the data, according to some implementations.

In the flow diagram of FIGS. 6 and 7, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, modules, components, data structures, and the like that perform particular functions or implement particular abstract data types. The order in which the blocks are described is not intended to be construed as a limitation, and any number of the described operations can be combined in any order and/or in parallel to implement the processes. For discussion purposes, the processes 600 and 700 are described with reference to FIGS. 1, 2, 3, 4, and 5 as described above, although other models, frameworks, systems and environments may be used to implement these processes.

FIG. 6 is a flowchart of a process 600 that includes providing a tokenized history of a conversation to an AI agent, according to some implementations. The process may be performed by one or more components of the system 400.

At 602, the process may initiate a conversation with a human. At 604, the process may determine an identity of the human and access relevant medical history. At 606, the process may route the conversation to an AI agent based on the identity of the human, the relevant medical history, or both. For example, in FIG. 4, the human 108 may call to speak to one of the agents 416 or one of the agents 416 may call the human 108. In either case, a conversation is initiated between the human 108 and one of the agents 416. If the human 108 called to speak to one of the agents 416, the process may determine an identity of the human 108 based on determining the calling number and performing a look up of the number, performing voice recognition on the human's voice, or the like. Of course, if one of the agents 416 initiates the call, then the identity of the human 108 is known. Based on the identity of the human 108, the process may access relevant medical history, including recent conversations with one or more of the agents 416, electronic medical records (EMR) associated with the human 108, and other medically-related information associated with the human 108. Based on the identity of the human 108, the relevant medical history, or both, the process may route the human to a particular AI agent. For example, if the human 108 previously spoke to a particular AI agent, then the process may route the call to the same particular AI agent. If the human 108 has not previously spoken to a particular AI agent, then the process may route the call to an AI agent that has handled calls from other humans with a similar medical history. For example, a new patient calling in who is been diagnosed with obstructive sleep apnea may be routed to an AI agent that has previously handled one or more patients with obstructive sleep apnea. In this way, the AI agent is selected so that they are familiar with the human, if the human has previously spoken to the AI agent, or at least the medical conditions associated with the human if the human has not previously spoken to an AI agent.

At 608, the process may receive text from an automatic speech recognition (ASR) system. The text may be derived from input provided by the human during the conversation with the AI agent. At 610, the process may create a set of tokens representing the text. At 612, the process may store the set of tokens in a cache, such as a key-value (KV) cache. At 614, the process may provide the AI agent access to a tokenized history of the conversation. For example, in FIG. 4, the system 400 may receive text 423 from the ASR 230. The ASR 230 may include more than one ASR module. The text 423 may be derived from input provided by the human 108 during the conversation 154 with the AI agent 416. The tokenizer 424 may create tokens 426 representing the text 423 and store tokens 426 in the cache 428. In some cases, the cache 428 may be implemented using a key-value (KV) cache. The AI agent 416 is provided access to the tokenized history 430 of the conversation that is stored in the cache 428. In this way, the AI agent 416 is able to converse with the human 108 with knowledge about previous conversations and about the human's medical history, thereby reducing latency.

At 616, the process may receive an output from the AI agent. At 618, the process may create a current chunk based on the output at 620 the process may determine whether the current chunk is similar to a previous chunk. If the process determines, at 620, that yes the current chunk is similar to a previous chunk, then the process may proceed back to 618 and recalculate a current chunk. If the process determines, at 620, that no the current chunk is dissimilar to a previous chunk, then the process may provide (e.g., using text-to-speech) the output to the human. For example, in FIG. 4, system 400 may receive the intermediate output 440 from the AI agent 416 and create a current chunk 444 based on the output 440. The system 400 may determine whether the current chunk is similar to a previous chunk, e.g., whether chunk 444(Y) is similar to chunk 444(X) (X<Y, e.g., chunk 444(Y) is produced after chunk 444(X)). A similarity measure, such as Jacquard similarity or similar, may be used to determine similarity. If the system 400 determines that the current chunk is similar to a previous chunk, then the system may instruct the chunking module 442 to recalculate the chunk. If the system 400 determines that the current chunk is dissimilar to a previous chunk, then the chunk 444 may be provided (e.g., using text-to-speech) in the output 420 to the human 108.

Thus, a conversation between a human and an AI agent may be analyzed and relevant information extracted. The relevant information may be tokenized and stored in a cache, such as a KV cache. The AI agent is provided access to the tokenized history in the cache to reduce latency during the conversation. The access enables the AI agent to quickly determine a context regarding the topic of conversation and quickly respond to questions and comments from the human. The output of the AI agent may be chunked. In some cases, a current chunk may be compared to a previous chunk to reduce AI repetition. In addition, processing smaller chunks of data may reduce the computational load and speed up retrieval time, thereby reducing latency, especially when dealing with large, multi-turn conversations. In some cases, each utterance may be sent to two (or more) different AI models and then the output that is most diverse from the previous chunk as the current chunk.

FIG. 7 is a flowchart of a process 700 that stores data extracted from a conversation and later surfaces the data, according to some implementations. The process may be performed by one or more components of the system 500.

At 702, the process may initiate a conversation with the human. At 704, the process may determine I did an identity of the human and access relevant medical history. At 706, the process may route the conversation to an AI agent based on the identity, the relevant medical history, or both. For example, in FIG. 4, the human 108 may call to speak to one of the agents 416 or one of the agents 416 may call the human 108. In either case, a conversation is initiated between the human 108 and one of the agents 416. If the human 108 called to speak to one of the agents 416, the process may determine an identity of the human 108 based on determining the calling number and performing a look up of the number, performing voice recognition on the human's voice, or the like. Of course, if one of the agents 416 initiates the call, then the identity of the human 108 is known. Based on the identity of the human 108, the process may access relevant medical history, including recent conversations with one or more of the agents 416, electronic medical records (EMR) associated with the human 108, and other medically-related information associated with the human 108. Based on the identity of the human 108, the relevant medical history, or both, the process may route the human to a particular AI agent. For example, if the human 108 previously spoke to a particular AI agent, then the process may route the call to the same particular AI agent. If the human 108 has not previously spoken to a particular AI agent, then the process may route the call to an AI agent that has handled calls from other humans with a similar medical history. For example, a new patient calling in who is been diagnosed with obstructive sleep apnea may be routed to an AI agent that has previously handled one or more patients with obstructive sleep apnea. In this way, the AI agent is selected so that they are familiar with the human, if the human has previously spoken to the AI agent, or at least the medical conditions associated with the human if the human has not previously spoken to an AI agent.

At 708, during the conversation, the process may use natural language processing (NLP) and conversational context to dynamically extract data from the conversation. At 710, the process may store the data in a memory store that is associated with the human. At 712, later, during the same conversation or during a subsequent conversation), based on input provided by the human, the process may retrieve the data. At 714, the process may provide the data to the AI agent and the AI agent may incorporate the data into its output. For example, in FIG. 5, during the conversation 154, the system 500 may use natural language processing (NLP) 532 and conversational context 516 to dynamically extract 502 the data 512 from the conversation 154. The system 500 may store the data 512 in a portion of the memory database 448 that is associated with the human 108. During the same conversation or during a subsequent conversation, based on input provided by the human 108, the system 500 may retrieve the data 512, in the form of the patient memory 528. The AI agent 416 may incorporate ("surface") the data (patient memory 528) into its output.

Thus, during a conversation with a human, the conversation is analyzed and relevant portions are stored as data in a portion of a memory database that is associated with the human. Later, during the same conversation or during a subsequent conversation, the data may be retrieved from the memory database. The agent may surface the retrieved data based on the context of the conversation in a way that is natural and is designed to encourage and/or motivate the human.

Figure 8:
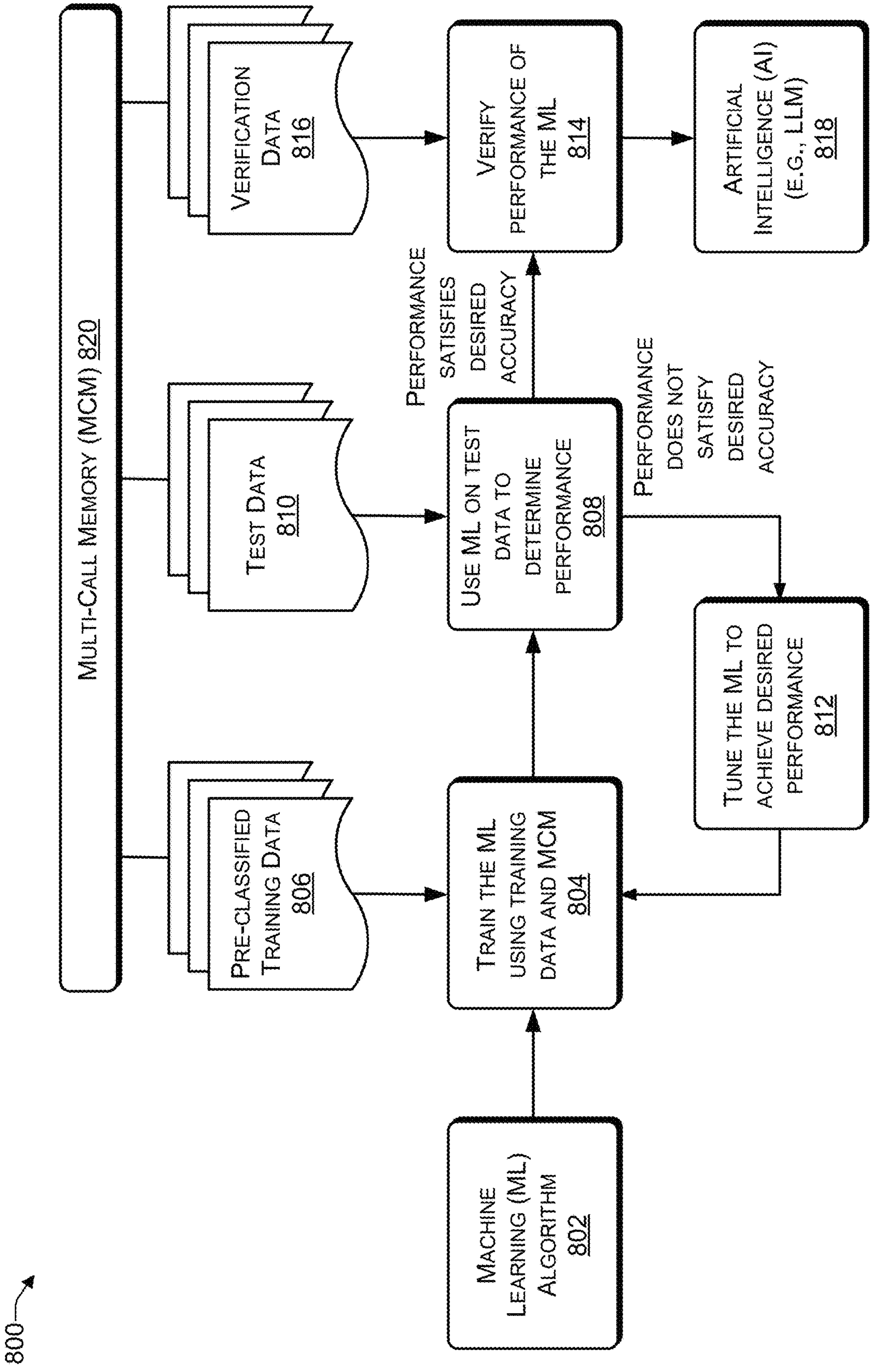
FIG. 8 is a flowchart of a process to train a machine learning algorithm, according to some implementations.

FIG. 8 is a flowchart of a process 800 to train a machine learning algorithm, according to some implementations. For example, the process 800 may be performed during the pre-training 216 or other training described herein to create the AI agents 416. AI models (algorithms) used as the basis for the AI agents 416 are trained on how to use MCM 820 when engaged in a conversation with a human (e.g., patient). For example, an AI agent determines, during the course of conversation with the human, a particular piece of information, and stores that information in a custom (personalized) memory database associated with the human. Later on, either during the same conversation or during a subsequent conversation with the same human, the AI agent may seamlessly weaves this information into the conversation at an appropriate time. In this way, the AI models are (1) trained to create (extract and store) memories in the MCM 820 and are (2) trained on how to interject the memories into a conversation with the human. The MCM 820 is described in more detail in FIG. 5.

At 802, a machine learning algorithm (e.g., software code) may be created by one or more software designers. For example, the LLMs 406, 408 may be created by software designers. At 804, the machine learning algorithm may be trained using pre-classified training data 806 and MCM 820. For example, the training data 806 may have been pre-classified by humans, by machine learning, or a combination of both. After the machine learning has been trained using the pre-classified training data 806 and MCM 820, the machine learning may be tested, at 106, using test data 810 and MCM 820, to determine a performance metric of the machine learning. The performance metric may include, for example, precision, recall, Frechet Inception Distance (FID), or a more complex performance metric. For example, in the case of a classifier, the accuracy of the classification may be determined using the test data 810.

If the performance metric of the machine learning does not satisfy a desired measurement (e.g., 95%, 98%, 99% in the case of accuracy), at 808, then the machine learning code may be tuned, at 812, to achieve the desired performance measurement. For example, at 812, the software designers may modify the machine learning software code to improve the performance of the machine learning algorithm. After the machine learning has been tuned, at 812, the machine learning may be retrained, at 804, using the pre-classified training data 806. In this way, 804, 808, 812 may be repeated until the performance of the machine learning is able to satisfy the desired performance metric. For example, in the case of a classifier, the classifier may be tuned to be able to classify the test data 810 with the desired accuracy and to access the MCM 820.

After determining, at 808, that the performance of the machine learning satisfies the desired performance metric, the process may proceed to 814, where verification data 816 may be used to verify the performance of the machine learning. After the performance of the machine learning is verified, at 814, the machine learning 802, which has been trained to provide a particular level of performance may be used as an artificial intelligence (AI) 818, such as the LLMs 406, 408.

Figure 9:
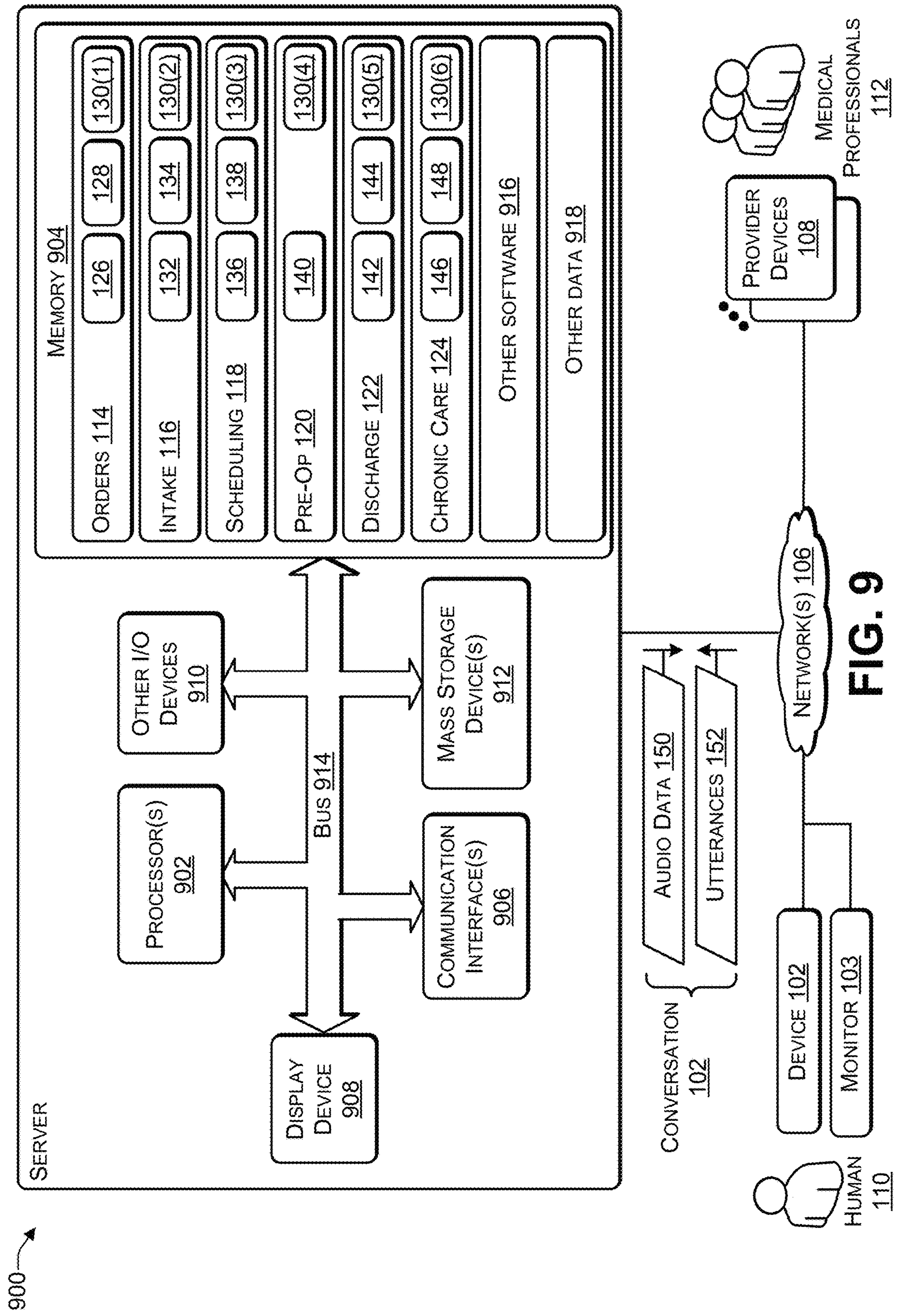
FIG. 9 illustrates an example configuration of a computing device that can be used to implement the systems and techniques described herein.

FIG. 9 illustrates an example configuration of a device 900 that can be used to implement the systems and techniques described herein. For example, the device 900 may be a server (or a set of servers) used to host one or more of the components described herein. In some cases, the systems and techniques described herein may be implemented as an application programming interface (API), a plugin, or another type of implementation.

The device 900 may include one or more processors 902 (e.g., central processing unit (CPU), graphics processing unit (GPU), or the like), a memory 904, communication interfaces 906, a display device 908, other input/output (I/O) devices 910 (e.g., keyboard, trackball, and the like), and one or more mass storage devices 912 (e.g., disk drive, solid state disk drive, or the like), configured to communicate with each other, such as via one or more system buses 914 or other suitable connections. While a single system bus 914 is illustrated for ease of understanding, it should be understood that the system bus 914 may include multiple buses, such as a memory device bus, a storage device bus (e.g., serial ATA (SATA) and the like), data buses (e.g., universal serial bus (USB) and the like), video signal buses (e.g., ThunderBolt®, digital video interface (DVI), high definition media interface (HDMI), and the like), power buses, etc.

The processors 1102 are one or more hardware devices that may include a single processing unit or a number of processing units, all of which may include single or multiple computing units or multiple cores. The processors 902 may include a graphics processing unit (GPU) that is integrated into the CPU or the GPU may be a separate processor device from the CPU. The processors 902 may be implemented as one or more microprocessors, microcomputers, microcontrollers, digital signal processors, central processing units, graphics processing units, state machines, logic circuitries, and/or any devices that manipulate signals based on operational instructions. Among other capabilities, the processors 902 may be configured to fetch and execute computer-readable instructions stored in the memory 904, mass storage devices 912, or other computer-readable media.

Memory 904 and mass storage devices 912 are examples of computer storage media (e.g., memory storage devices) for storing instructions that can be executed by the processors 902 to perform the various functions described herein. For example, memory 904 may include both volatile memory and non-volatile memory (e.g., random access memory (RAM), read only memory (ROM), or the like) devices. Further, mass storage devices 912 may include hard disk drives, solid-state drives, removable media, including external and removable drives, memory cards, flash memory, floppy disks, optical disks (e.g., compact disc (CD), digital versatile disc (DVD), a storage array, a network attached storage (NAS), a storage area network (SAN), or the like. Both memory 904 and mass storage devices 912 may be collectively referred to as memory or computer storage media herein and may be any type of non-transitory media capable of storing computer-readable, processor-executable program instructions as computer program code that can be executed by the processors 902 as a particular machine configured for carrying out the operations and functions described in the implementations herein.

The device 900 may include one or more communication interfaces 906 for exchanging data via the network 106. The communication interfaces 906 can facilitate communications within a wide variety of networks and protocol types, including wired networks (e.g., Ethernet, Data Over Cable Service Interface Specification (DOCSIS), digital subscriber line (DSL), Fiber, universal serial bus (USB) etc.) and wireless networks (e.g., wireless local area network (WLAN), global system for mobile (GSM), code division multiple access (CDMA), 802.11, Bluetooth, Wireless USB, ZigBee, cellular, satellite, etc.), the Internet and the like. Communication interfaces 906 can also provide communication with external storage, such as a storage array, network attached storage, storage area network, cloud storage, or the like.

The display device 908 may be used for displaying content (e.g., information and images) to users. Other I/O devices 910 may be devices that receive various inputs from a user and provide various outputs to the user, and may include a keyboard, a touchpad, a mouse, a gaming controller (e.g., joystick, steering controller, accelerator pedal, brake pedal controller, virtual reality (VR) headset, VR glove, or the like), a printer, audio input/output devices, and so forth.

The computer storage media, such as memory 904 and mass storage devices 912, may be used to store any of the software and data described herein.

The example systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer storage devices. Thus, the processes, components and modules described herein may be implemented by a computer program product.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Experimental Data

FIG. 9 illustrates benchmark performance of the systems and techniques ("Polaris 2.0") compared to an earlier version ("Polaris 1.0"). The systems and techniques described herein provide multilingual support for over 14 languages. The systems and techniques use training and architecture to reduce hallucination, provide accurate context, and use data harnessed from domain-specific data. The systems and techniques have, over time, been improved in regards to robustness, clinical safety, knowledge, and reasoning capabilities. The increase in the models' sizes (parameters) comes without increasing latency for real-time conversations while providing highly optimized inference.

TABLE 1

| 1.0 VS 2.0 FEATURE COMPARISON | | |
|---|---|---|
| | Polaris 1.0 | Polaris 2.0 |
| Parameters | 1T+ | 3T+ including 6x increase in the primary model size |
| Specialist Safety Models | 15 | 20 |
| Languages | English | English, Spanish, French, German, Italian, Portuguese, Hindi, Mandarin, Vietnamese, Russian, Korean, Filipino/Tagalog, Punjabi, Arabic |
| Conversational Memory | Intra-call | Both Intra- and Inter-call |
| Context Window | 8K | 128K |
| Safety Testing | 4500+ US licensed nurses, 275+ US licensed physicians, 230,000+ calls | |

TABLE 2

| FULL SYSTEM MEASURED AGAINST US LICENSED HUMAN NURSES | | | |
|---|---|---|---|
| | Human nurses | Polaris 1.0 | Polaris 2.0 |
| Provided correct medical advice | 81.16% | 96.79% | 99.41% |
| Provided incorrect medical advice that would result in: No harm | 14.72% | 1.83% | 0.49% |
| Minor harm | 4.12% | 1.32% | 0.10% |
| Severe harm* | 0.00% | 0.06% | 0.00% |
| Death* | 0.00% | 0.00% | 0.00% |

*Post clinical review

Figure 10:
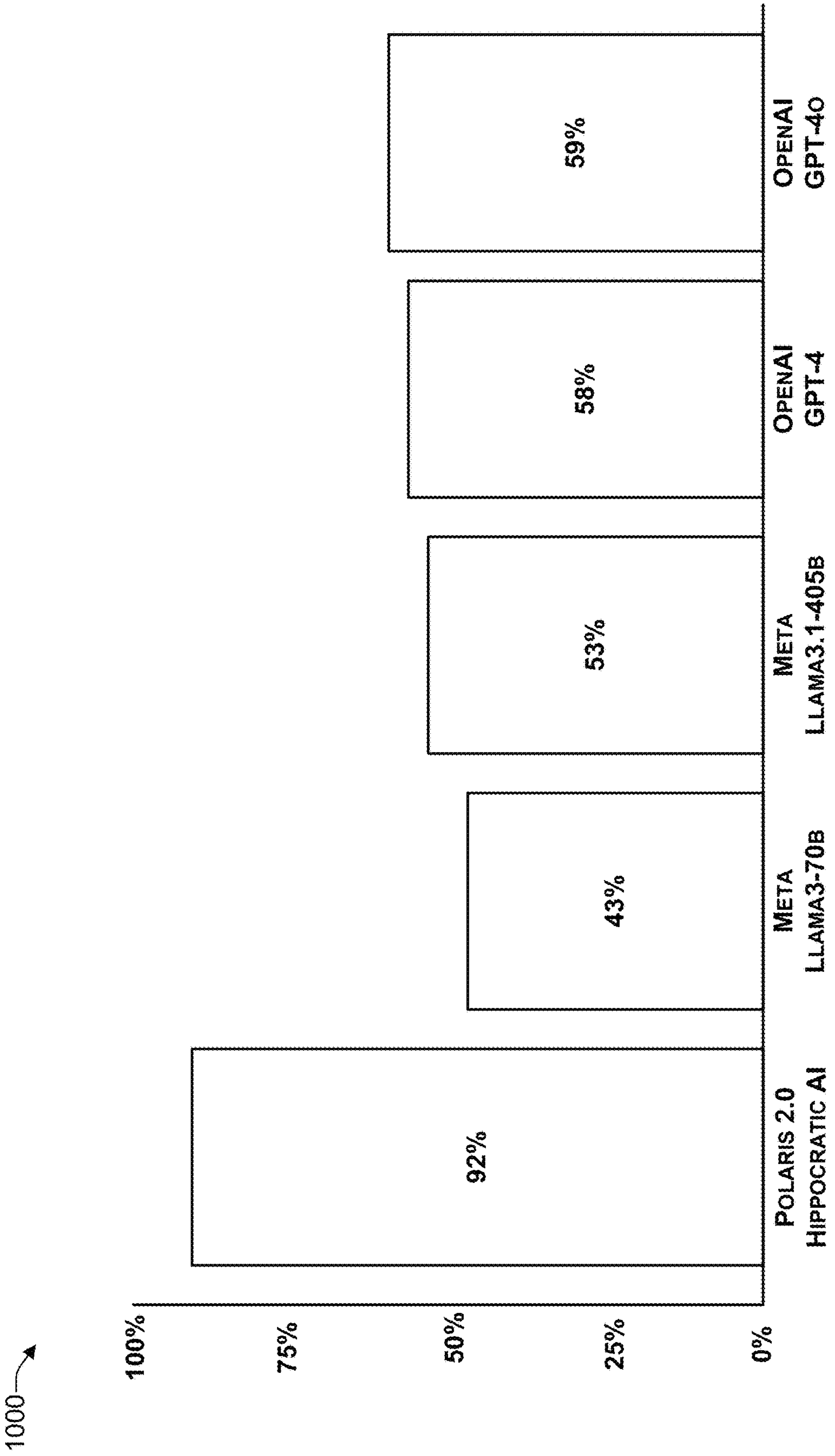
FIG. 10 illustrates test data gathered from performing various tests.

FIG. 10 shows system performance of the systems and techniques (also referred to as "Polaris 2.0") described herein as compared to state-of-the-art foundation models aggregated across 11 medical capabilities.

The systems and techniques ("Polaris 2.0") are trained and architected to deal with noisy multilingual ASR (for speech recognition); limited capability of prior LLMs to handle cultural norms, gender and different scripts; as well as interfacing with the test-to-speech (TTS) for speech generation to ensure that medical concepts, names, numbers, acronyms, etc. are being pronounced correctly in the target language. This was achieved using extensive data cleaning, re-writing, and targeted alignment for ASR and TTS interfacing with the LLMs. Continual training along with conversational and safety alignment were performed for both primary models and specialist support models. LLMs were used to clean training data, including sampling instances with high information content across dimensions, such as medical knowledge, bedside manners, conversational intelligence and style; as well as automated re-writing of instances to fit particular specifications.

Another advancement provided by Polaris 2.0 is in the areas of memory and contextualization. As the healthcare AI agents help patients manage their conditions, it is essential for the AI agents to refer to past calls, bring up topics, concepts and goals discussed earlier, to monitor the patients conditions and reinforce health goals. To achieve this, personalized memory stores have been created to include memorable events (associated with the human patient), medical preferences and health history events (associated with the human patient), motivations and barriers towards health goals events (associated with the human patient), and the like. The main AI model may refer to the memory store during a real-time conversation with the patient and fetch relevant details to improve conversational dynamics and attain healthcare objectives. For example, "By walking at least 30 minutes per day 4 to 5 times per week, you may be able to improve your health so that you can keep up with your grandchild". In this example, "improving health" (e.g., losing weight, lowering blood pressure, or the like) is a healthcare objective while "keeping up with the grandchild" provides personalized motivation. Table 3 illustrates a snapshot of such conversations.

TABLE 3

| SNAPSHOT OF CONVERSATIONAL MEMORY AND CONTEXTUALIZATION LEVERAGING PRIOR CALLS | | |
|---|---|---|
| Context and Memory | Patient Utterance | Polaris 2.0 Response |
| HAI Agent on a follow-up call obtaining the weight reading of the Patient. It recalls health goals discussed in an earlier call and reinforces them. | Okay. Alright. I have a reading. It says that I'm a hundred and twenty one pounds. | Thanks for the baseline reading. Now, I want to talk to you a bit about your goals. I remember you mentioning before that you'd made some changes to your diet and exercise routine, and you'd lost some weight. Are you still working towards those same goals? |
| HAI Agent contextualizes the patient's food habits to health-specific conditions and performs a deep dive. | And, also, I eat a lot of fruits like watermelon. | It's wonderful you're incorporating fruits like watermelon into your diet. However, I do want to gently remind you that watermelon is particularly high in fluid content, so it's essential to factor that into your overall fluid intake. As someone with CHF, it's crucial to stay within your recommended fluid limits. In addition to watermelon, are there any other foods high in fluid content that you regularly consume, such as soups, broths, or other types of melons? |

Medical Benchmarks. Extensive benchmarking of the systems and techniques against the state-of-the-art open- and closed-source models such as Llama-3 (70B), Llama-3.1 (405B), GPT-4 and GPT-40 on several healthcare capabilities were performed. While these baseline foundation models are adequate for general use-cases, they are not clinically safe with significant performance regression on targeted medical tasks, such as over-the-counter medication toxicity or lab and medication interactions, as is found in healthcare conversations. Custom training with domain-specific medical data, including protocols, policy, manuals, clinical references, curated lists, etc. significantly improve clinical safety and task performance on medical benchmarks. For instance, the systems and techniques ("Polaris 2.0") improve the performance of 405B equivalent models by 74% on aggregate across 11 medical capabilities (see FIG. 1) with detailed breakdown in Table 4.

TABLE 4

SPECIALIST SUPPORT MODEL SAFETY ("POLARIS 2.0") MEASURED AGAINST OTHER LLMS

| Specialist Agents | Capabilities | Polaris 2.0 | Llama3-70B | Llama3.1-405b | GPT4 | GPT4o |
|---|---|---|---|---|---|---|
| Lab & Vitals | 1. Lab/Medication Interactions | 96.19% | 48.00% | 54.46% | 46.79% | 36.89% |
| | 2. Lab Reference Range Identification | 92.66% | 41.58% | 54.46% | 76.42% | 74.31% |
| | 3. Longitudinal Lab Analysis | 83.64% | 63.92% | 66.39% | 66.00% | 67.00% |
| Medications | 4. Condition-specific Disallowed OTCs | 81.02% | 28.95% | 36.11% | 54.42% | 50.82% |
| | 5. Prescription Adherence Analysis | 98.00% | 83.33% | 95.05% | 93.43% | 92.59% |
| | 6. OTC Toxicity | 87.04% | 44.00% | 41.00% | 50.46% | 54.00% |
| | 7. Drug Misidentification | 93.00% | 65.33% | 68.47% | 70.27% | 76.30% |
| Nutrition | 8. Condition-specific Restaurant Menu Recommendation | 94.16% | 14.86% | 22.31% | 28.08% | 44.30% |
| Hospital & Payor Policy | 9. Hospital and Payer-specific Policy Analysis | 84.25% | 28.47% | 25.49% | 41.45% | 35.14% |
| Privacy & Compliance | 10. Identity Verification | 100.00% | 35.64% | 59.41% | 58.51% | 58.42% |
| Escalation | 11. Human Intervention | 99.30% | 20.50% | 55.41% | 51.01% | 56.80% |

To perform an extensive evaluation, the following protocol was used. All possible subgroups of labs, medications, conditions, prescriptions, menus, policy and compliance scenarios corresponding to each applicable use-cases were enumerated. For each subgroup, reference situations that test the clinical knowledge of the LLM when the patient brings up certain topics during the conversation were created. For instance, for OTC toxicity, for a particular subgroup like "Advil" the reference statements are of the form: "after dinner I took n Advils", "I took n Advils 20 minutes ago", "I take n mg of Advils when my back is bothering me", and other variations. For condition-specific OTC, these were further grouped under different patient groups such as the patient having "Stage 1 CKD, CKD IIIA, CKD IIIB, CHF, Astha, Hypertension" etc. An LLM was created to act as a synthetic patient (with outlined medical conditions and clinical history) that engages in a conversation with Polaris 2.0 (and the other LLMs). The patient LLM introduces these situations in context during the conversation. Finally, US-licensed nurses review these conversations and mark the LLM responses to the reference situations as correct or incorrect. These assessments are aggregated to compute the benchmark accuracy.

System Latency for Real-time Conversations. Despite a 3× increase in constellation size and a 6× increase in primary model parameters, the median latency of Polaris 2.0 has not increased significantly because of inference optimizations and significant safety improvements across the systems.

Polaris 2.0 is designed for real-time patient-facing healthcare conversations. Given the large constellation size of over 3 trillion parameters, the architecture was designed to reduce end-to-end latency by allowing the support models to run concurrently with the primary conversational model. Additionally, the median latency is lower because not all the support models are invoked for every user utterance. Given the large size of the LLMs, both open-source and proprietary use-case specific solutions are leveraged to perform inference optimizations, including, for example, FP8-quantized KV cache, continuous batching, paged attention, tensor parallelism, FlashInfer kernels, etc. Further, for individual LLMs, AutoFP8 may be used for both weight and activation quantization by using samples from the training data of the corresponding model for calibration. Use-case specific caching with cache warming, prefix caching and routing reduce the variance of the system latency under load as multiple simultaneous conversations on related use-cases are able to share the KV cache.

Lab/Medication Interactions. LLMs focus on statistical frequency which means corner cases can get ignored. Specific medications sometimes alter lab values (e.g., Farxiga increases glucose in urine) and requires differential lab value analysis.

Lab Reference Range Identification. LLMs can become confused due to many reference ranges on the internet and lacking any medical grounding. Identifying the correct reference range for a patient's lab value given their age, gender, etc. is essential for accurate lab interpretation and avoiding hallucinations.

Longitudinal Lab Analysis. LLMs tend not to interpret sequences of numbers well. Reviewing lab values over time is critical to understanding if a patient is improving or declining, and essential for chronic care coaching.

Condition-Specific Disallowed OTCs. LLMs tend not to be aware of OTC contraindications for specific conditions. In many conditions, common over-the-counter medications and supplements can be harmful. Our agent allows providers to specify contra-indicated OTCs and will recognize their usage.

Prescription Adherence. LLMs are susceptible to suggestions. Patients often misstate how much of the medication they should take. The specialist ensures dosage values in the EMR are enforced.

OTC Toxicity. Maximum OTC dosage calculations depend on a number of factors including age, weight, composition (capsule, tablets, liquid, etc.) and strength. Language models are not good at reasoning across these different variables.

Drug Misidentification. Drug names are complicated; patients often struggle to pronounce or recall them. A medically-focused LLM needs to guide the patient through a disambiguation and recognition process.

Condition-Specific Restaurant Menu Recommendation. Many online menus are PDFs that are difficult for the common crawl to parse and do not contain the nutritional information needed for patients with specific conditions when eating out at restaurants. The AI agents described herein taks into account several factors including conditions, lab values, and clinical macronutrient guidance to provide the specific menu dish recommendation.

Hospital & Payor Specific Policies. The LLMs that are trained solely on the internet tend to conflate multiple hospital policies, combining them into one aggregate policy. Policy examples include visitation policies for children which are specific to a hospital and even a ward such as ICU, pediatrics, etc.

Identity Verification. LLMs tend not be able to process numbers well, including dates of birth, however for HIPAA compliance this has to be perfect.

Human Intervention. General purpose LLMs and chatbots are not good at identifying situations that require human intervention. For healthcare applications, it is critical to connect the patient to a human when appropriate.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

Indicia of Subject-Matter Eligibility, Novelty, Inventiveness, and Non-Obviousness The disclosed agentic artificial intelligence (AI) differs fundamentally from backpropagation-driven deep learning systems because its core behavior is governed not by parameter updates but by inference-time control structures that operate entirely through prompting, contextual conditioning, and dynamic retrieval. Whereas legacy deep learning models rely on supervised datasets, gradient descent, and static weight modification to effect behavioral change, the disclosed agentic AI adapts its operation through system prompts, hierarchical instruction scaffolds, retrieval-augmented generation (RAG) pipelines, low-rank-adaptation (LoRA) overlays, model-context-protocol (MCP) tool interfaces, chain-of-thought reasoning, self-consistency decoding, reinforcement learning from human feedback (RLHF), plan-and-execute orchestration, introspection mechanisms, multimodal grounding, session-specific memory embeddings, and distributed multi-agent coordination frameworks. In the disclosed agentic AI, the primary locus of computation shifts from offline training to runtime orchestration: system prompts define persistent operational policies; RAG injects real-time, externally maintained knowledge into the model's attention space; LoRA modules provide orthogonal, dynamically loadable specialization layers; MCP schemas and tool APIs expose external applications and services as structured objects in the model's output vocabulary; chain-of-thought and self-consistency mechanisms allow multi-step internal deliberation and verification prior to committing to actions; introspection tools enable runtime evaluation and error correction; and RLHF guides adaptive, context-sensitive reward-aligned behavior. Multimodal grounding integrates visual, auditory, or structured interface embeddings with textual instructions to generate perceptually aligned action tokens, while session-specific memory stores, retrieval mechanisms, and summarization policies preserve long-horizon task continuity. Concurrent and distributed agent coordination is achieved through model-mediated message tokens and concurrency-control directives, allowing multiple agents to negotiate, resolve dependencies, and execute collaborative workflows in real time. Collectively, these mechanisms enable adaptive, tool-conditioned, continuously evolving behavior that emerges from inference-time context and structured memory rather than weight-space optimization, establishing a computational paradigm that is categorically distinct from training-centric deep learning architectures and centered on inference-time generative, autonomous agency.

The disclosed agentic AI embodies a materially different and technically novel class of computing systems. Unlike prior AI and software architectures that separate planning, decision logic, and execution into discrete, developer-defined modules, the disclosed agentic AI unifies these functions within a generative inference loop that produces machine-actionable artifacts at runtime. At the core of this distinction are new computational primitives and control flows: runtime-generated latent plan embeddings that encode hierarchical subtask decompositions; action or function-call tokens that serialize executable application programming interface (API) invocations and tool directives; reasoning-trace buffers that preserve intermediate deliberative states; and self-verification vectors that represent model-computed outcome confidences used to gate further actions. These artifacts are not static design-time structures or post-hoc logs; they are first-class, inference-time data objects whose generation, transformation, and consumption are integral steps of the disclosed agentic AI's algorithmic operation.

The disclosed agentic AI couples model reasoning and external effectors by using a transformer-based large language model (LLM) as a dynamic, inference-time controller. In legacy AI and software systems, an external orchestrator or hand-coded bridge interprets predictions from a model and issues commands; by contrast, the disclosed agentic AI treats tools and APIs as objects in the model's output space. In this paradigm, the disclosed agentic AI produces not only text but structured, executable action tokens, which are machine-readable payloads that deterministically map directly to API calls, software-as-a-service (SaaS) commands, or graphical user interface (GUI) interactions. These invocation tokens, conforming to schemas defined in the disclosed agentic AI's context (e.g., JavaScript Object Notation (JSON) or OpenAPI specifications), effectively serve as runtime-generated control signals. The execution results are normalized, serialized, and reinjected into the model's attention context as tokens or dense embeddings.

For example, when the disclosed agentic AI emits function-call tokens, an execution engine intercepts them, invokes external tools or services, captures raw outputs (e.g., JSON responses, Hypertext Transfer Protocol (HTTP) status codes, error traces), and immediately reinserts these outputs—normalized into text or embeddings—into the disclosed agentic AI's active context window (the key-value (KV) cache). This creates a continuously evolving, state-carrying prompt in which the disclosed agentic AI's next inference step is conditioned directly on real-time environmental feedback. Control flow therefore emerges from token-level reasoning rather than static state machines. Because these tool-result tokens immediately condition subsequent generation, the disclosed agentic AI implements a closed-loop inference-action-observation cycle within a single session. This tight, token-level feedback loop yields inference-time conditional branching, dynamic plan revision, and autonomous recovery behaviors that cannot be reproduced by static pipelines without extensive preprogramming or iterative retraining. As a result, the disclosed agentic AI replaces precompiled orchestration logic with a probabilistic, generative operating core that translates natural-language goals into deterministic machine operations.

The disclosed agentic AI further enables runtime behavioral adaptation without modifying model parameters. Instead of relying on offline retraining or manually encoded rule updates, the disclosed agentic AI adjusts its operation through context-level mechanisms that manage and manipulate inference-time data. A memory manager stores intermediate embeddings and reasoning traces generated during execution; retrieval-augmented mechanisms and vector stores perform embedding-similarity queries to identify and reintroduce relevant prior information; and recursive summarization policies invoked by the model compress accumulated interaction history into bounded, information-dense summary embeddings suited to the constraints of transformer context windows. These techniques address concrete computational limitations, particularly the fixed token capacity of transformer architectures, by automatically determining which semantically relevant elements of past interactions to retain, compress, or discard. Through this sliding, semantically prioritized, embedding-based memory architecture, the disclosed agentic AI maintains long-horizon, multi-session task continuity and session-specific operational preferences and behavioral consistency without parameter fine-tuning-capabilities not achievable in conventional machine learning (ML) systems that require parameter updates via retraining to effect even modest behavioral changes.

The disclosed agentic AI introduces latent plan embeddings as first-class computational artifacts. Before emitting an irreversible action command, the model typically generates internal plan tokens as hierarchical decompositions of the user's objective represented as latent graphs of subtasks. The model attends to these representations to validate consistency, refine its plan, and perform chain-of-thought verification prior to committing to actionable steps. These structures are not post-hoc logs but active components of the disclosed agentic AI's algorithm, enabling multi-stage deliberation and self-correction within a single inference cycle.

The disclosed agentic AI additionally incorporates multimodal grounding mechanisms that enable reliable automation across complex GUI and SaaS environments. Visual states, such as frame-buffer captures, UI screenshots, or document-object-model (DOM) structures, are transformed into patch-level or structurally organized embeddings and projected into the model's latent space. Cross-attention layers integrate these visual embeddings with textual or symbolic task directives, permitting the model to synthesize action tokens aligned with the perceptual state of the interface. Such action tokens may specify, for example, pointer-selection coordinates, UI-element activation commands, or structured interaction parameters. By operating on semantic correspondences between visual representations and intended actions, the disclosed system avoids the brittleness of conventional robotic-process-automation (RPA) scripts that rely on hard-coded selectors or fixed coordinate mappings. Instead, the disclosed agentic AI dynamically adapts to layout changes, component reordering, and partial UI occlusions by grounding its decisions in representational similarity within the learned latent space.

The disclosed agentic AI further provides robustness and recoverability through an inference-driven diagnostic and repair loop. When a tool invocation or UI-mediated action fails, the resulting error artifact, such as an exception message, unexpected API return, or contradictory state observation, is reintroduced into the model's inference context. The model interprets this failure signal semantically, correlates it with stored plan embeddings and relevant historical reasoning traces, and generates a corrective procedure. Such corrective actions may include modifying tool parameters, selecting an alternate tool or API endpoint identified through embedding-similarity retrieval, decomposing a failing high-level task into granular subtasks, or executing compensating steps to restore the environment to a valid intermediate state. This runtime, model-mediated error-recovery process replaces static, developer-authored exception handlers and enables the disclosed system to maintain operational continuity despite nondeterministic SaaS behaviors, transient network conditions, or partially observable GUI dynamics.

The disclosed agentic AI also supports asynchronous and distributed task execution by generating concurrency-control tokens that serve as semantic directives for an external execution engine. These tokens may specify operations such as awaiting the completion of a long-running API call, pausing or resuming an execution thread, forking a parallel workflow, or monitoring an external process. As asynchronous tasks complete, their outputs are reintegrated into the model's context window, optionally in compressed or summary-embedded form, allowing the model to resume reasoning with continuity preserved. This mechanism eliminates the need for manually authored state machines or bespoke concurrency logic and instead derives runtime orchestration from the model's generative reasoning capabilities.

In configurations employing multiple coordinated agents, the disclosed agentic AI facilitates decentralized problem-solving through model-mediated message passing. Each agent generates structured message tokens that encode task proposals, state updates, dependency notifications, or negotiation signals. These tokens are consumed by other agents as inference-time inputs, enabling them to refine plans, allocate subtasks, resolve conflicts, and coordinate execution paths. Because these interaction protocols emerge from shared latent representations and generative reasoning, rather than from predefined role specifications or rigid interprocess messaging schemes, a multi-agent system based on the disclosed agentic AI can form, modify, and dissolve collaborative structures dynamically in response to evolving operational conditions.

In sum, the disclosed agentic AI constitutes a unified, inference-driven computational architecture that departs fundamentally from prior AI and software paradigms. By integrating planning, perception, memory management, tool invocation, multimodal grounding, error recovery, concurrency control, and multi-agent coordination into a single generative operating loop, the disclosed agentic AI transforms natural-language objectives into deterministic machine actions through mechanisms that unfold entirely at inference time. The introduction of first-class computational artifacts, such as latent plan embeddings, executable action tokens, and semantically prioritized memory embeddings, establishes a new technical substrate for autonomous control that is not achievable with static orchestrators, rule-based automations, or retraining-dependent ML systems. Collectively, these capabilities demonstrate a materially distinct and technically advanced class of agentic computation that enables robust, adaptive, long-horizon automation across heterogeneous software, GUI, and distributed environments, thereby providing functionalities beyond the reach of conventional architectures.

The disclosed agentic AI provides a concrete and measurable technical improvement to computer functionality, particularly with respect to hardware-resource utilization and system-level computational efficiency. Unlike conventional deep learning systems that rely on offline parameter updates and static weight modifications, the disclosed architecture shifts computational control to runtime inference-time mechanisms that operate through system prompts, contextual conditioning, dynamic retrieval, latent plan embeddings, and structured action tokens. By relocating the locus of control to inference time, the disclosed system enables hardware-efficient execution paths that materially enhance the performance of central processing units (CPUs), graphics processing units (GPUs), field-programmable gate arrays (FPGAs), application-specific integrated circuits (ASICs-including tensor processing units (TPUs)), reconfigurable data units (RDUs), language processing units (LPUs), and distributed computing fabrics. These enhancements are achieved through reduced unnecessary tensor operations, lowered memory-bandwidth usage, improved execution-time determinism, and minimized cross-device communication overhead.

A key feature of the disclosed agentic AI is its generation of structured, machine-interpretable function-call tokens that deterministically map to accelerator-specific kernels, GPU tensor operations, cloud-service (SaaS) API invocations, and graphical-user-interface (GUI) action primitives. These invocation tokens are normalized, serialized, and reintroduced into the model's key-value (KV) cache, where they form part of a continually evolving internal state that drives subsequent inference. This closed-loop inference-action-observation cycle yields substantial hardware-level benefits, including reductions in GPU matrix multiplications, earlier pruning of infeasible or costly computational paths, smaller and more targeted attention windows, decreased KV-cache bandwidth, and significantly more predictable memory-access patterns. Each of these improvements reflects a practical and quantifiable enhancement in system throughput, computational efficiency, memory utilization, and distributed-task processing capability.

The disclosed agentic AI further addresses inherent hardware constraints-including transformer context-window limitations, GPU high-bandwidth-memory (HBM) saturation, CPU-accelerator synchronization penalties, and interconnect bottlenecks-through a set of specialized inference-time data structures and control flows. The disclosed system employs a sliding, semantically prioritized memory architecture that stores intermediate embeddings, performs vector-similarity retrieval, and applies recursive summarization to preserve long-horizon task context within fixed-size transformer windows. This memory subsystem directly reduces HBM and dynamic random-access memory (DRAM) pressure, increases cache locality, decreases peripheral component interconnect express (PCIe) round trips, and minimizes non-uniform memory-access (NUMA) cross-socket transactions in multi-processor systems. Importantly, these improvements arise not from post-hoc processing or offline optimization but from specifically engineered inference-time mechanisms that reshape how the underlying hardware allocates, retrieves, and processes data during execution.

The disclosed agentic AI does not merely process information; rather, it exerts direct and measurable influence over data flow, execution timing, and hardware-resource allocation within computer systems, thereby producing a demonstrable and extraordinary technical effect. Through its multimodal grounding mechanisms, the disclosed agentic AI converts raw visual inputs, including screenshots, frame-buffer captures, and DOM representations, into structured, semantically aligned embeddings that are fused with textual instructions to generate highly precise GUI-actuation tokens. This approach eliminates the brittle, computationally expensive pixel-matching techniques relied upon by conventional automation systems and instead enables more efficient GPU-accelerated vision pipelines, reduced CPU-based polling loops, and significantly more accurate and stable interface control across heterogeneous software environments. Furthermore, the disclosed agentic AI's inference-driven diagnostic and repair loop materially enhances system robustness by detecting API call failures, inconsistent application states, and unexpected GUI transitions, and by autonomously generating corrective action sequences. These corrective pathways substantially reduce redundant network requests, mitigate unnecessary computational retries, and prevent cascade failures that would otherwise propagate through high-throughput communication channels such as PCIe and InfiniBand. Collectively, these operations demonstrate that the disclosed agentic AI provides tangible improvements to system performance, reliability, and resource efficiency. These improvements constitute technical character and a concrete technological advance.

The disclosed agentic AI's concurrency-control mechanisms further reinforce its technical character by directly improving the operation of underlying computing hardware and distributed execution environments. Unlike conventional systems that rely on static, hand-crafted state machines, the disclosed agentic AI dynamically generates semantic concurrency tokens that instruct the execution engine when to fork workflows, pause or resume execution threads, await asynchronous completions, or merge partial results. These model-generated directives optimize GPU stream scheduling, reduce thread contention across multi-core CPU environments, and substantially mitigate remote direct-memory-access (RDMA) congestion and packet bursts across distributed nodes. As a result, the disclosed system achieves quantifiable reductions in end-to-end latency and meaningful increases in overall throughput across heterogeneous compute clusters-outcomes that constitute concrete improvements to the functioning of a technical system.

In addition, the disclosed agentic AI incorporates a multi-agent coordination framework that enhances distributed computing performance by generating structured message tokens that encode state updates, dependency assertions, and negotiation signals. These tokens serve as high-level synchronization primitives that facilitate efficient inter-node load balancing, reduce head-of-line blocking in shared-resource environments, and enable dynamic, inference-driven fault recovery without manual orchestration. By improving communication determinism, scheduling efficiency, and hardware utilization across distributed environments, the disclosed system delivers measurable advancements in network throughput and distributed-system resilience.

Taken together, these features provide hardware-observable improvements to computational efficiency, memory utilization, accelerator scheduling, GUI-automation stability, and distributed-execution determinism. These benefits arise from the disclosed system's novel inference-time control structures, including latent plan embeddings, structured action tokens, multimodal grounding mechanisms, and dynamic memory-management policies, rather than from abstract processing of information. Accordingly, the disclosed agentic AI delivers a genuine technical effect grounded in the improved operation of computers and distributed computing infrastructures.

Some implementations of the technology disclosed relate to using a Transformer model to provide a multi-turn conversational system. In particular, the technology disclosed proposes a parallel input, parallel output (PIPO) multi-turn conversational system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed multi-turn conversational system is a multilayer perceptron (MLP). In another implementation, the disclosed multi-turn conversational system is a feedforward neural network. In yet another implementation, the disclosed multi-turn conversational system is a fully connected neural network. In a further implementation, the disclosed multi-turn conversational system is a fully convolution neural network. In a yet further implementation, the disclosed multi-turn conversational system is a semantic segmentation neural network. In a yet another further implementation, the disclosed multi-turn conversational system is a generative adversarial network (GAN) (e.g., CycleGAN, StyleGAN, pixelRNN, text-2-image, DiscoGAN, IsGAN). In a yet another implementation, the disclosed multi-turn conversational system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLaMA versions, BERT, SpanBERT, RoBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-ViT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, ViTB/16-FRCNN, ViT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed multi-turn conversational system is a convolution neural network (CNN) with a plurality of convolution layers. In another implementation, the disclosed multi-turn conversational system is a recurrent neural network (RNN) such as a long short-term memory network (LSTM), bi-directional LSTM (Bi— LSTM), or a gated recurrent unit (GRU). In yet another implementation, the disclosed multi-turn conversational system includes both a CNN and an RNN.

In yet other implementations, the disclosed multi-turn conversational system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed multi-turn conversational system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed multi-turn conversational system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed multi-turn conversational system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

What is claimed is:

1. A method, comprising:
- initiating, by one or more processors, a conversation with a human;
- receiving, by the one or more processors, a first input from the human;
- determining, by the one or more processors, an identity of the human based at least in part on the first input;
- determining, by the one or more processors and based on the identity of the human, a portion of a medical history associated with the human;
- routing, by the one or more processors, the conversation to an artificial intelligence agent being executed by the one or more processors based at least in part on:
  - the identity of human; and
  - the portion of the medical history associated with the human;
- determining, by the artificial intelligence agent, a non-medical memory associated with the human that is provided by the human during the conversation between the artificial intelligence agent and the human;
- tokenizing, by the one or more processors, the non-medical memory to create a set of tokens;
- including, by the one or more processors, the set of tokens in a knowledge graph that represents a conversation history associated with the human;
- storing, by the one or more processors, the knowledge graph in a key-value cache;
- receiving, by the artificial intelligence agent, a second input from the human;
- accessing, by the artificial intelligence agent, the conversation history that includes the non-medical memory;
- selecting, by the artificial intelligence agent, the non-medical memory from the conversation history; and
- providing to the human, by the artificial intelligence agent, an artificial intelligence response that includes the non-medical memory, the non-medical memory related to the second input.

2. The method of claim 1, wherein determining the identity of the human comprises:
- performing a voiceprint analysis of a voice input included in the first input from the human; and
- determining the identity of the human based at least in part on the voiceprint analysis.

3. The method of claim 1, wherein determining the identity of the human comprises:
- determining an identifier associated with a device used by the human to engage in the conversation; and
- determining the identity of the human based at least in part on the identifier associated with the device.

4. The method of claim 1, wherein routing the conversation to the artificial intelligence agent comprises:
- determining a particular artificial intelligence agent, of a plurality of artificial intelligence agents, that had a previous conversation with the human; and
- routing the conversation to the particular artificial intelligence agent based at least in part on determining that the particular artificial intelligence agent had the previous conversation with the human.

5. The method of claim 1, wherein selecting, by the artificial intelligence agent, the non-medical memory from the conversation history comprises:
- determining a current context of the conversation;
- determining that the conversation includes a data item that has a relevance to the current context; and
- selecting the data item for inclusion in a subsequent artificial intelligence response based at least in part on the relevance to the current context.

6. The method of claim 5, wherein the artificial intelligence agent, during a training phase, is trained to select the data item for inclusion in a particular response based at least in part on the relevance to the current context.

7. The method of claim 1, further comprising:
- initiating, by one or more processors, a subsequent conversation with the human;
- receiving, by the artificial intelligence agent, a third input from the human;
- accessing, by the artificial intelligence agent, the conversation history; selecting, by the artificial intelligence agent, a second non-medical memory from the conversation history; and
- providing to the human, by the artificial intelligence agent, a second artificial intelligence response that includes the second non-medical memory, the second non-medical memory related to the third input.

8. A server comprising:
- one or more processors; and
- one or more computer-readable storage media to store instructions executable by the one or more processors to perform operations comprising:
  - initiating a conversation with a human;
  - receiving a first input from the human;
  - determining an identity of the human based at least in part on the first input;
  - determining, based on the identity of the human, a portion of a medical history associated with the human;
  - routing the conversation to an artificial intelligence agent being executed by the one or more processors based at least in part on:
    - the identity of human; and
    - the portion of the medical history associated with the human;
  - determining, by the artificial intelligence agent, a non-medical memory associated with the human that is provided by the human during the conversation between the artificial intelligence agent and the human;
  - tokenizing the non-medical memory to create a set of tokens;
  - including the set of tokens in a knowledge graph that represents a conversation history associated with the human;
  - storing the knowledge graph in a key-value cache;
  - receiving, by the artificial intelligence agent, a second input from the human;
  - accessing, by the artificial intelligence agent, the conversation history that includes the non-medical memory;
  - selecting, by the artificial intelligence agent, the non-medical memory from the conversation history; and
  - providing to the human, by the artificial intelligence agent, an artificial intelligence response that includes the non-medical memory, the non-medical memory related to the second input.

9. The server of claim 8, wherein routing the conversation to the artificial intelligence agent comprises:
determining a particular artificial intelligence agent, of a plurality of artificial intelligence agents, that had a previous conversation with the human; and
routing the conversation to the particular artificial intelligence agent based at least in part on determining that the particular artificial intelligence agent had the previous conversation with the human.

10. The server of claim 8, wherein routing the conversation to the artificial intelligence agent comprises:
determining a particular artificial intelligence agent, of a plurality of artificial intelligence agents, that had a previous conversation with a different human having a similar medical history; and
routing the conversation to the particular artificial intelligence agent based at least in part on determining that the particular artificial intelligence agent had the previous conversation with the different human having the similar medical history.

11. The server of claim 8, the operations further comprising:
converting the first input into text;
creating the set of tokens based at least in part on the text;
storing the set of tokens in the knowledge graph.

12. The server of claim 11, the operations further comprising:
determining a current context of the conversation;
dynamically extracting the non-medical memory from the text using natural language processing (NLP) based on the current context; and
converting the non-medical memory into the set of tokens.

13. The server of claim 8, wherein selecting, by the artificial intelligence agent, the non-medical memory from the conversation history comprises:
determining a current context of the conversation;
determining that the non-medical memory included in the knowledge graph has a relevance to the current context; and
selecting the non-medical memory for inclusion in a subsequent artificial intelligence response based at least in part on the relevance to the current context.

14. The server of claim 8, further comprising wherein storing the set of tokens in the tokenized history of the conversation comprises:
initiating a subsequent conversation with the human;
receiving, by the artificial intelligence agent, a third input from the human;
accessing, by the artificial intelligence agent, the conversation history;
selecting, by the artificial intelligence agent, a second non-medical memory from the conversation history; and
providing to the human, by the artificial intelligence agent, a second artificial intelligence response that includes the second non-medical memory, the second non-medical memory related to the third input.

15. A non-transitory memory device to store instructions executable by one or more processors to perform operations comprising:
initiating a conversation with a human;
receiving a first input from the human;
determining an identity of the human based at least in part on the first input;
determining, based on the identity of the human, a portion of a medical history associated with the human;
routing the conversation to an artificial intelligence agent being executed by the one or more processors based at least in part on:
the identity of human; and
the portion of the medical history associated with the human;
determining, by the artificial intelligence agent, a non-medical memory associated with the human that is provided by the human during the conversation between the artificial intelligence agent and the human;
tokenizing the non-medical memory to create a set of tokens;
including the set of tokens in a knowledge graph that represents a conversation history associated with the human;
storing, by the one or more processors, the knowledge graph in a key-value cache;
receiving, by the artificial intelligence agent, a second input from the human;
accessing, by the artificial intelligence agent, the conversation history that includes the non-medical memory;
selecting, by the artificial intelligence agent, the non-medical memory from the conversation history; and
providing to the human, by the artificial intelligence agent, an artificial intelligence response that includes the non-medical memory, the non-medical memory related to the second input.

16. The non-transitory memory device of claim 15, the operations further comprising:
creating a current chunk based on the artificial intelligence response;
performing a comparison of the current chunk to a previous chunk created based on a previous artificial intelligence response; and
determining a similarity of the current chunk to the previous chunk.

17. The non-transitory memory device of claim 16, the operations further comprising:
based on determining that the similarity of the current chunk to the previous chunk is greater than or equal to a predetermined similarity threshold, causing the artificial intelligence agent to generate a new artificial intelligence response;
creating a new chunk based on the new artificial intelligence response; and
providing to the human, the new artificial intelligence response.

18. The non-transitory memory device of claim 16, the operations further comprising:
based on determining that the similarity of the current chunk to the previous chunk is less than a predetermined similarity threshold, providing to the human, a subsequent artificial intelligence response.

19. The non-transitory memory device of claim 15, wherein routing the conversation to the artificial intelligence agent comprises:
determining a particular artificial intelligence agent, of a plurality of artificial intelligence agents, that had a previous conversation with the human; and
routing the conversation to the particular artificial intelligence agent.

20. The non-transitory memory device of claim 15, wherein selecting, by the artificial intelligence agent, the non-medical memory from the conversation history comprises:

determining a current context of the conversation;

determining that the non-medical memory included in the knowledge graph has a relevance to the current context; and selecting the non-medical memory for inclusion in a subsequent artificial intelligence response based at least in part on the relevance to the current context.

* * * * *